 United States Patent
Gill et al.

(10) Patent No.: US 7,813,791 B1
(45) Date of Patent: Oct. 12, 2010

(54) SYSTEMS AND METHODS FOR EMPLOYING AN FFT TO DISTINGUISH R-WAVES FROM T-WAVES USING AN IMPLANTABLE MEDICAL DEVICE

(75) Inventors: Jong Gill, Valencia, CA (US); Peter Boileau, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 550 days.

(21) Appl. No.: 11/841,350

(22) Filed: Aug. 20, 2007

(51) Int. Cl.
*A61B 5/0456* (2006.01)
(52) U.S. Cl. .............................. 600/521; 607/1; 607/2; 600/508; 600/509; 600/515
(58) Field of Classification Search ......... 600/508–509, 600/515, 521; 607/1–2; 128/899, 920, 923–924
See application file for complete search history.

(56) References Cited

U.S. PATENT DOCUMENTS

| | | | |
|---|---|---|---|
| 4,680,708 A | 7/1987 | Ambos et al. | |
| 5,292,348 A | 3/1994 | Saumarez et al. | |
| 5,404,880 A | 4/1995 | Throne | |
| 5,609,158 A | 3/1997 | Chan | |
| 5,623,936 A | 4/1997 | McClure | |
| 5,749,901 A | 5/1998 | Bush et al. | |
| 5,772,604 A | 6/1998 | Langberg et al. | |
| 6,064,906 A | 5/2000 | Langberg et al. | |
| 6,249,705 B1 | 6/2001 | Snell | |
| 6,415,179 B1 | 7/2002 | Pendekanti et al. | |
| 6,445,949 B1 | 9/2002 | Kroll | |
| 6,650,931 B1 | 11/2003 | McClure et al. | |
| 6,772,007 B1 | 8/2004 | Kroll | |
| 6,823,213 B1 | 11/2004 | Norris et al. | |

(Continued)

FOREIGN PATENT DOCUMENTS

WO  9119452  12/1991

(Continued)

OTHER PUBLICATIONS

Gilliam, F. Roosevelt III, "T-Wave Overseeing in Implantable Cardiac Defibrillators Is Due to Technical Failure of Device Sensing," J Cardiovasc Electrophysiol. May 2006;17:553-556.

(Continued)

*Primary Examiner*—Carl H Layno
*Assistant Examiner*—Deborah Malamud

(57) ABSTRACT

A Fast Fourier Transform (FFT) converts time-varying event waveforms into the frequency domain waveforms to thereby decompose the events into their spectral components, which are analyzed to distinguish R-waves from T-waves. In some embodiments, the FFT is only activated if a ventricular tachyarrhythmia is already indicated. For example, an initial ventricular rate may be derived from a ventricular IEGM based on all events detected therein. The initial ventricular rate is compared against one or more thresholds representative of ventricular tachycardia (VT) and/or ventricular fibrillation (VF) to determine if VT/VF is indicated. If so, the FFT is activated to distinguish R-waves from T-waves and, in particular, to detect and eliminate T-wave oversensing. Then, the ventricular rate is re-determined based only on the rate of true R-waves. Therapy is delivered if VT/VF is still detected.

26 Claims, 14 Drawing Sheets

U.S. PATENT DOCUMENTS

| | | | |
|---|---|---|---|
| 6,907,286 | B1 | 6/2005 | Kroll et al. |
| 6,980,860 | B2 | 12/2005 | Stadler et al. |
| 6,993,388 | B2 | 1/2006 | Bullinga |
| 7,031,770 | B2 | 4/2006 | Collins et al. |
| 7,117,030 | B2 | 10/2006 | Berenfeld et al. |
| 2003/0055345 | A1 | 3/2003 | Eigler et al. |
| 2004/0059237 | A1* | 3/2004 | Narayan et al. ............ 600/509 |
| 2004/0077962 | A1 | 4/2004 | Kroll |
| 2005/0027202 | A1 | 2/2005 | Ginzburg et al. |
| 2006/0122526 | A1 | 6/2006 | Berenfeld et al. |

FOREIGN PATENT DOCUMENTS

| | | |
|---|---|---|
| WO | 9741773 | 11/1997 |
| WO | 2005006209 A1 | 1/2005 |

OTHER PUBLICATIONS

Grimm, W. et al., "Electrocardiographically Documented Unnecessary, Spontaneous Shocks in 241 Patients with Implantable Cardioverter Defibrillators," PACE. Nov. 1992(Pt 1);15:1667-1773.

Rinaldi, C.A. et al. "A 17 year experience of inappropriate shock therapy in patients with implantable cardioverter-defibrillators: are we getting any better?" Heart 2004;90;330-331.

Weretka, Slawomir et al., "Ventricular Oversensing: A Study of 101 Patients Implanted with Dual Chamber Defibrillators and Two Different Lead Systems." PACE. Jan. 2003(Pt 1);26:65-70.

Washizuka, Takashi MD et al., "Inappropriate Discharges by Fourth Generation Implantable Cardioverter Defibrillators in Patients with Ventricular Arrhythmias." Jpn Circ J. 2001;65:927-930.

* cited by examiner

SYSTEMS AND METHODS FOR EMPLOYING AN FFT TO DISTINGUISH R-WAVES FROM T-WAVES USING AN IMPLANTABLE MEDICAL DEVICE

CROSS-REFERENCE TO RELATED APPLICATIONS

This application is related to copending U.S. patent application Ser. No. 11/841,243, filed concurrently herewith, titled "Systems and Methods for Employing an FFT to Detect Atrial Fibrillation Using an Implantable Medical Device".

FIELD OF THE INVENTION

The invention generally relates to implantable medical devices such as pacemakers and implantable cardioverter/defibrillators (ICDs) and, in particular, to techniques for distinguishing R-waves from T-waves to prevent T-wave oversensing and to facilitate reliable detection of ventricular tachyarrhythmias.

BACKGROUND OF THE INVENTION

An arrhythmia is an abnormal heart beat pattern. One example of arrhythmia is bradycardia wherein the heart beats at an abnormally slow rate or wherein significant pauses occur between consecutive beats. Other examples of arrhythmia include tachyarrhythmias wherein the heart beats at an abnormally fast rate. With an atrial tachyarrhythmia, such as atrial tachycardia (AT), the atria of the heart beat abnormally fast. With a ventricular tachyarrhythmia, such as ventricular tachycardia (VT), the ventricles of the heart beat abnormally fast. Though often unpleasant for the patient, a tachycardia is typically not fatal. However, some tachycardias, particularly ventricular tachycardia, can trigger ventricular fibrillation (VF) wherein the heart beats chaotically such that there is little or no net flow of blood from the heart to the brain and other organs. VF, if not terminated, is fatal. Hence, it is highly desirable for implantable medical devices, such as pacemaker or ICDs (herein generally referred to as a pacer/ICD) to detect arrhythmias, particularly ventricular tachyarrhythmias, so that appropriate therapy can be automatically delivered by the device.

To detect arrhythmias, the pacer/ICD senses electrical cardiac signals within the heart of the patient using one or more implanted electrodes. The cardiac signals are sensed within the device by one or more sense amplifiers and then filtered by various filters configured so as to extract signals of interest, such as signals indicative of bradycardia or tachycardia or other arrhythmias. To this end, state-of-the-art pacer/ICDs are often provided with a wideband filter and two narrow bandwidth filters. The wideband filter eliminates low and high frequency noise but otherwise retains all features of the cardiac signals indicative of actual electrical events within the heart of the patient. That is, the wideband filter retains P-waves, R-waves and T-waves, whether occurring at normal heart rates, excessively low rates, or excessively high rates. The P-wave is the portion of an intracardiac electrogram (IEGM) signal that is representative of the electrical depolarization of the atria and is thus also representative of the physical contraction of the atria. The R-wave is the portion of the IEGM that is representative of the electrical depolarization of the ventricles and is thus also representative of the physical contraction of the ventricles. The T-wave is the portion of the IEGM that is representative of the electrical repolarization of the ventricles. (Note that the repolarization of the atria typically generates electrical signals that are too weak to be detected and hence atrial repolarization events are not typically detected by pacer/ICDs.)

Hence, within the wideband cardiac signals, the P-wave is typically followed by the R-wave, which is then followed by the T-wave. Note, however, that the wideband filter also retains signals associated with any chaotic or random beating of the chambers of the heart, particularly signals associated with VF, which may not be easily categorized as having discrete P-waves, R-waves or T-waves. Insofar as the R-wave is concerned, strictly speaking, the portion of the IEGM corresponding to the depolarization of the ventricles is referred to as the QRS complex, with the R-wave representing only a portion of that complex. However, the terms R-wave and QRS-complex are often used interchangeably in the literature when applied to the IEGM. Herein, the term "R-wave" is used to refer to the entire QRS-complex, unless otherwise noted.

FIG. 1 provides a stylized illustration of a cardiac signal 2 corresponding to a single heartbeat, particularly illustrating the R-wave 4 and the T-wave 6. In practice, the relative magnitudes of the various events can differ significantly. In some cases, the T-wave may be as large as or larger than the R-wave. Accordingly, it can be difficult to distinguish R-waves from T-waves from the wideband-filtered signals so as to obtain an accurate measure of the ventricular rate, and so it can be difficult to reliably detect either bradycardia or tachycardia from the wideband-filtered signals. Hence, the specialized narrowband filters are provided. A first narrowband filter, herein referred to as a bradycardia filter, is configured to filter the cardiac signal output from the sense amplifier so as to facilitate detection of only those features of the cardiac signals indicative of ventricular bradycardia. In particular, the bradycardia filter is designed to filter out substantially all portions of the cardiac signal not associated with non-VF R-waves. R-waves occurring during VF typically have a frequency too high to be detected by the bradycardia filter. Thus, the bradycardia filter provides an output signal that retains only relatively "slow" R-waves and eliminates substantially everything else (P-waves, T-waves, noise, etc.) from the raw cardiac signal sensed by the sense amplifiers. Bradycardia can thereby be conveniently detected by examining the filtered signal. If the rate at which R-waves appear in the filtered signal is below a lower rate threshold, or if no R-waves are present at all, then the patient is likely suffering an episode of bradycardia, and appropriate therapy can be delivered, such as demand-based pacing.

Advantageously, because all other features of the cardiac signals besides R-waves are filtered out by the bradycardia filter (i.e. T-waves, P-waves, noise, etc.), the sensitivity of the bradycardia filter can be set quite high so as to permit detection of even very low amplitude R-waves. The high sensitivity of the bradycardia filter thus substantially eliminates the risk of any possible undersensing of the R-waves (or at least any significant undersensing of non-VF R-waves.) Herein, "undersensing" refers to the failure to detect events of interest that are actually present within the raw cardiac signals. Meanwhile, the elimination of all other features of the cardiac signal by the filtering process (i.e. the elimination of P-waves, T-waves, etc.), means that there is little or no risk of "oversensing" of those other events when using the bradycardia filter. Herein, "oversensing" refers to the erroneous detection of an event not actually present in the raw cardiac signal, such as the detection of R-waves that are actually T-waves. Oversensing typically arises when one event is misidentified as another, as may occur, e.g., if a T-wave is improperly identified as an R-wave. As can be appreciated, T-wave oversensing is a significant concern since misidentification of T-waves as R-waves can result in significant miscalculation of the true heart rate within the patient, causing therapy to be delivered when not warranted or potentially causing therapy to be withheld even when needed.

A second narrowband filter, herein referred to as a tachycardia filter, is configured to filter the cardiac signal output from the sense amplifier so as to facilitate detection of only those features of the cardiac signals indicative of ventricular tachycardia. In particular, the tachycardia filter is designed to filter out substantially all portions of the cardiac signal not associated with relatively high rate R-waves, i.e. fast R-waves occurring at a rate consistent with VT of VF. Tachycardia can thereby be detected by examining the filtered signal. If the rate at which R-waves appear in the filtered signal is above a VT threshold, then the patient is likely suffering an episode of tachycardia, and appropriate therapy can be delivered, such as antitachycardia pacing (ATP) or shock. However, unlike the bradycardia filter, which fully eliminates T-waves, the tachycardia filter retains at least a portion of the T-wave. This is due to the fact that the frequencies associated with the fast R-waves of interest during VT are also associated with T-waves, and hence the filter cannot eliminate all T-waves while still retaining the R-waves. As such, the sensitivity of the tachycardia filter must be set so as to detect R-waves while eliminating T-waves. This is difficult, at best, since the relative magnitudes of the R-waves and T-waves may change significantly over time within the patient, perhaps due to the use of medications or due to physiological or anatomical changes in the heart brought on by medical conditions, such as cardiac ischemia, myocardial infarctions, congestive heart failure, etc. Moreover, as already noted, T-waves can sometimes have a magnitude that equals or exceeds that of the R-wave. Hence, T-wave oversensing is a significant problem within the tachycardia-filtered signals. If T-wave oversensing occurs, the ventricular rate cannot be accurately and reliably measured based solely on the output of the tachycardia filter (at least at the high rates associated with VT/VF), and hence problems arise in the detection of VT, VF or other forms of ventricular tachyarrhythmia. Failure to properly detect VT/VF when it is present can result in a failure to deliver appropriate therapy. False detection of VT/VF when it is not present can result in delivery of inappropriate therapy. As can be appreciated, both situations are of significant concern.

In view of the foregoing problems, it is highly desirable to provide improved techniques for reliably distinguishing different types of cardiac events within electrical cardiac signals and, in particular, to distinguish R-waves from T-waves so as to reduce or eliminate T-wave oversensing and thereby facilitate reliable detection of ventricular tachyarrhythmias. It is to this end that various aspects of the invention are generally directed.

SUMMARY OF THE INVENTION

In an exemplary embodiment of the invention, a method is provided for use by an implantable medical device for distinguishing cardiac events sensed by the device. Time-varying electrical cardiac signals are sensed within a patient in which the device is implanted, such as IEGMs. Time-varying cardiac event waveforms are identified therein, such as the waveforms of ventricular events not yet specifically identified as R-waves or T-waves. The time-varying waveforms are then converted into frequency-domain waveforms to extract the spectral components of the events. Then, different types of cardiac events are distinguished from one another based on the spectral components of the events. In one particular example, a Fast Fourier Transform (FFT) device is used to convert the time-varying waveforms into the frequency domain to decompose the events into their spectral components, which are then analyzed to distinguish R-waves from T-waves. An FFT is particularly efficient in converting time domain waveforms into frequency domain signals so that spectral components of events can be analyzed for use in distinguishing R-waves from T-waves. However, other suitable time-domain (TD) to frequency domain (FD) conversion or transformation devices or techniques can instead be employed.

In some embodiments, the TD to FD conversion is only performed if ventricular tachyarrhythmia is already indicated. For example, an initial ventricular rate may be derived from the ventricular IEGM based on all events detected therein. The initial ventricular rate is compared against one or more thresholds representative of VT and/or VF to determine if ventricular tachyarrhythmia is indicated. If so, the FFT is applied to the ventricular IEGM to distinguish R-waves from T-waves and, in particular, to detect and eliminate T-wave oversensing. Then, the ventricular rate is re-determined based only on the rate of true R-waves. Therapy is delivered if ventricular tachyarrhythmia is still detected. In this manner, the FFT is only used when warranted based on high ventricular rates, thereby reducing the processing and energy consumption burdens on the implanted device, while still gaining the benefits of spectral decomposition. In one particular example, the initial ventricular rate is compared against upper and lower VF thresholds of, e.g., 167 beats per minute (bpm) and 220 bpm, respectively. If the rate exceeds the upper VF threshold, the defibrillation capacitors are charged and defibrillation shocks are delivered as soon as possible, without activating the FFT. If the rate falls between the upper and lower VF threshold, the defibrillation capacitors are charged and, while they are being charged, the device activates the FFT to distinguish between R-waves and oversensed T-waves. Defibrillation shocks are only delivered if the ventricular rate still exceeds the lower VF threshold after T-wave oversensing is eliminated or, in some examples, only if the ventricular rate exceeds the upper VF threshold. The initial ventricular rate may also be compared against a still lower VT threshold set, e.g., to 120 bpm with ATP therapy activated if the ventricular rate still exceeds the VT threshold even after T-wave oversensing is eliminated.

A variety of techniques may be employed for distinguishing R-waves from T-waves based on the spectral components of the event derived from the FFT. In a first example, the implanted device determines an amount of power within a given ventricular event at frequencies exceeding a predetermined threshold frequency, such as 25 Hz. The implanted device identifies the event as being an R-wave if the amount of power above the frequency threshold exceeds a power threshold indicative of R-waves and identifies the event as being a T-wave otherwise. In this regard, there is typically little or no power in T-waves at frequencies exceeding 25 Hz, whereas there is considerable power at R-waves even well above 25 Hz. In a second example, the implanted device determines an amount of power at a particular test frequency, such as 50 Hz. The implanted device identifies the event as being an R-wave if the amount of power at the test frequency exceeds a power threshold indicative of R-waves and identifies the event as being a T-wave otherwise. In a third example, the implanted device determines an amount of power within a predetermined frequency band, such as from 30 Hz to 60 Hz. The implanted device identifies the event as being an R-wave if the amount of power within the frequency band exceeds a power threshold indicative of R-waves and identifies the event as being a T-wave otherwise. In a fourth example, the implanted device uses a linear discriminant analyzer (LDA) that has been trained to distinguish R-waves from T-waves based on their spectral components.

Preferably, the implanted device determines suitable comparison values (i.e. frequency threshold values, power threshold values and/or LDA weight values) in advance for use within a particular patient for use in distinguishing R-waves from T-waves within the patient. In one example, the implanted device detects and distinguishes R-waves and T-waves within an initial quiescent period within the patient using otherwise conventional techniques. The device processes the R-waves and T-waves of the quiescent period using the FFT and then determines suitable comparison values for distinguishing R-waves from T-waves based on spectral characteristics of the events. Once the comparison values have been determined within the initial quiescent period, the values can be applied, adjusted if appropriate, for use during episodes of possible ventricular tachyarrhythmia.

Exemplary techniques are also provided for detecting T-wave oversensing once R-waves have been distinguished from T-waves based on their spectral components. In one example, the implanted device detects sequences of alternating R-waves and T-waves in tachycardia-filtered signals (i.e. within signals that should exhibit only R-waves). The device associates such a sequence of alternating R-waves and T-waves as being indicative of T-wave oversensing and adjusts the sensitivity of the tachycardia filter in an attempt to eliminate further T-wave oversensing.

Thus, a variety of techniques are provided for reliably distinguishing between R-waves and T-waves so as to reduce or eliminate T-wave oversensing and thereby facilitate reliable detection of VT/VF. The various techniques can be selectively combined to further improve the specificity with which R-waves and T-waves are distinguished. For example, both power-based and LDA-based techniques may be exploited. The various techniques may be implemented, where appropriate, as systems, methods or other appropriate embodiments.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 2:
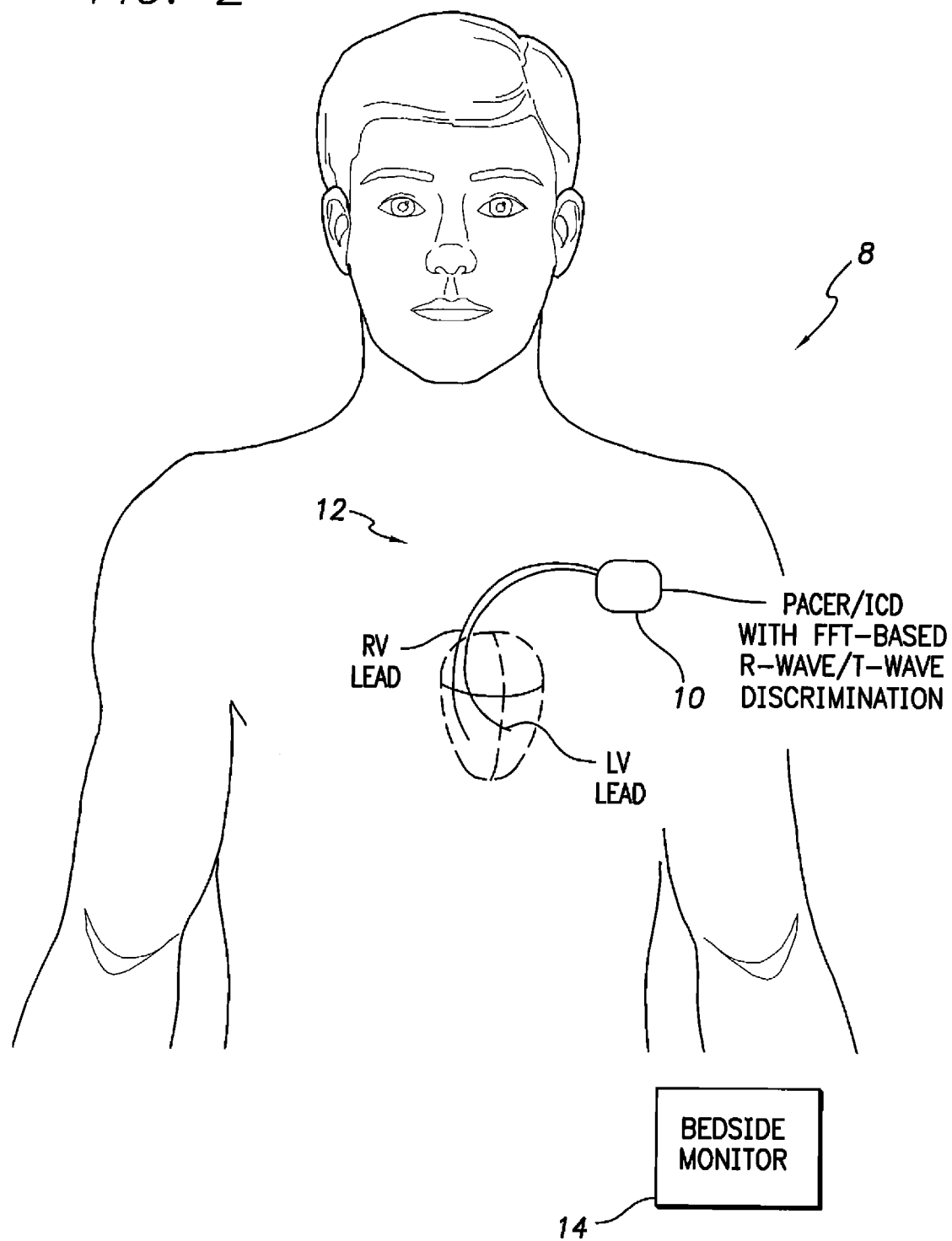
FIG. 2 illustrates pertinent components of an implantable medical system having a pacer/ICD capable of distinguishing R-waves and T-waves based on their spectral components.
Figure 14:
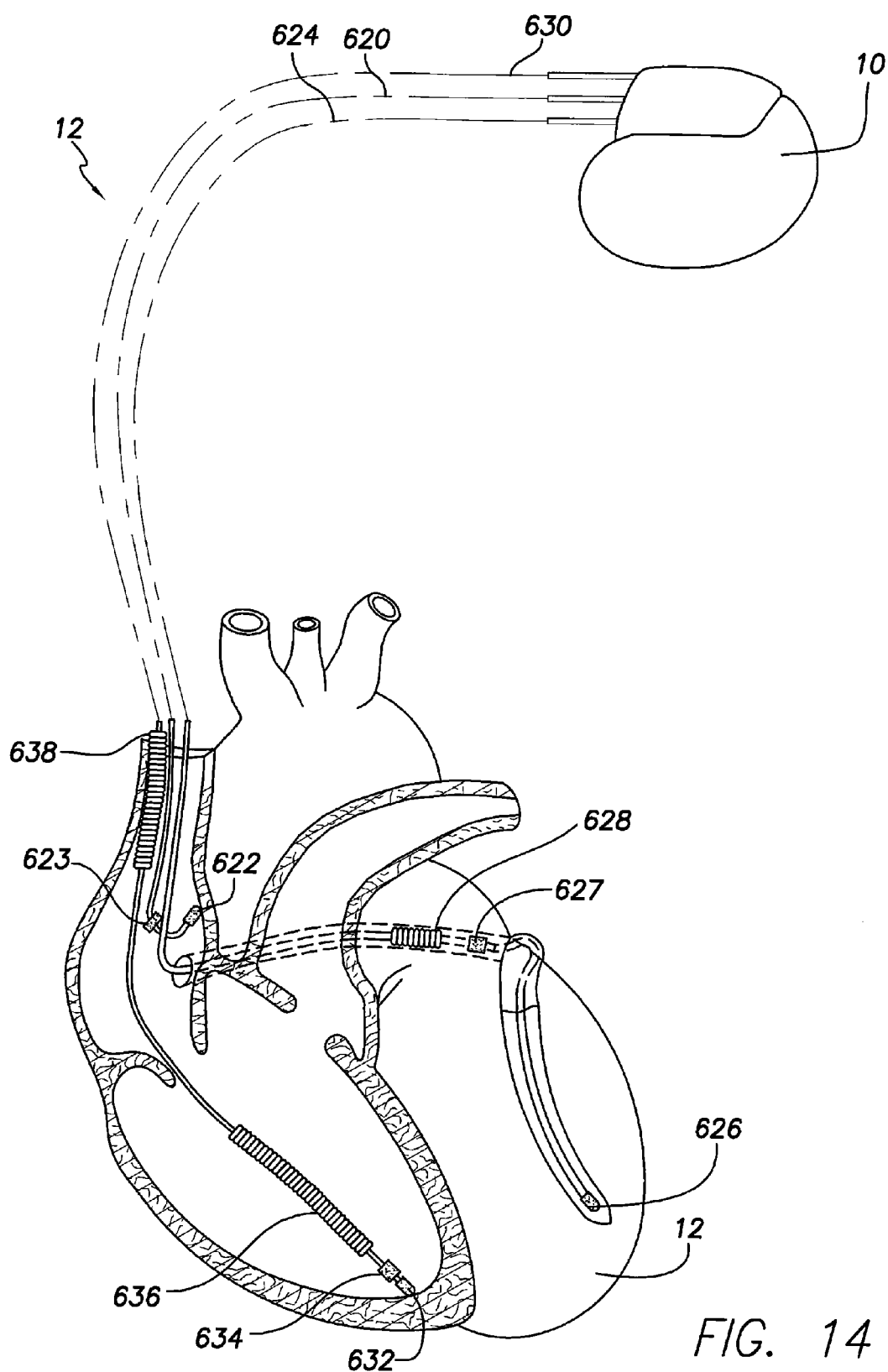
FIG. 14 is a simplified, partly cutaway view, illustrating the pacer/ICD of FIG. 2 along with a set of leads implanted in the heart of a patient.

FIG. 2 illustrates an implantable medical system 8 having a pacer/ICD 10 that includes an FFT-based R-wave/T-wave discrimination system, i.e., a system capable of distinguishing R-waves from T-waves using an FFT or other device for converting time-domain waveforms to frequency-domain waveforms. To this end, pacer/ICD 10 receives voltage signals from various cardiac pacing/sensing leads 12 (only two of which are shown in the FIG. 2) from which various channels of IEGM signals are derived including, for example, atrial IEGM (A-IEGM) signals and ventricular IEGM (V-IEGM) signals. A complete set of exemplary pacing leads are shown in FIG. 14 from which a wide variety of specific channels of IEGM signals may be derived. The V-IEGM signals are filtered using, at least, a narrowband tachycardia filter to generate filtered signals containing ventricular event waveforms of initially unknown types, i.e. the events are either ventricular depolarization events (R-waves) or ventricular repolarization events (T-waves). The waveforms are applied to an FFT to decompose the events into their spectral components, which the pacer/ICD analyzes to distinguish R-waves from T-waves, to identify T-wave oversensing, and to confirm ventricular arrhythmias, using techniques to be described in detail below.

The pacer/ICD is also capable of delivering therapy in response to tachyarrhythmias, such as delivery of ATP in response to VT or the delivery of high voltage defibrillation shocks in response to VF. Diagnostic information pertaining to any detected tachyarrhythmias and to the detection of any T-wave oversensing may be stored within the pacer/ICD for transmission to a bedside monitor 14, if one is provided, or for subsequent transmission to an external programmer (not shown in FIG. 2) for review by a physician or other medical professional. The physician may then prescribe any other appropriate therapies to prevent additional episodes of tachyarrhythmias. The physician may also adjust the operation of the pacer/ICD to activate, deactivate or otherwise control any therapies that are automatically applied and to adjust the operation of the tachycardia filter, if needed, to address any T-wave oversensing problems. The bedside monitor may be directly networked with a centralized computing system, such as the HouseCall™ system of St. Jude Medical, for promptly notifying the physician of any abnormal conditions, particularly any life-threatening ventricular tachyarrhythmias. Networking techniques for use with implantable medical systems are set forth, for example, in U.S. Pat. No. 6,249,705 to Snell, entitled "Distributed Network System for Use with Implantable Medical Devices."

Thus, FIG. 2 provides an overview of an implantable medical system capable of using an FFT to distinguish R-waves from T-waves to identify T-wave oversensing and to facilitate the reliable detection of tachyarrhythmias and for delivering therapy in response thereto. Although a pacer/ICD is illustrated in FIG. 2, it should be understood that the techniques of the invention may be implemented within other implantable medical devices.

Overview of Spectral Analysis-Based Techniques

Figure 3:
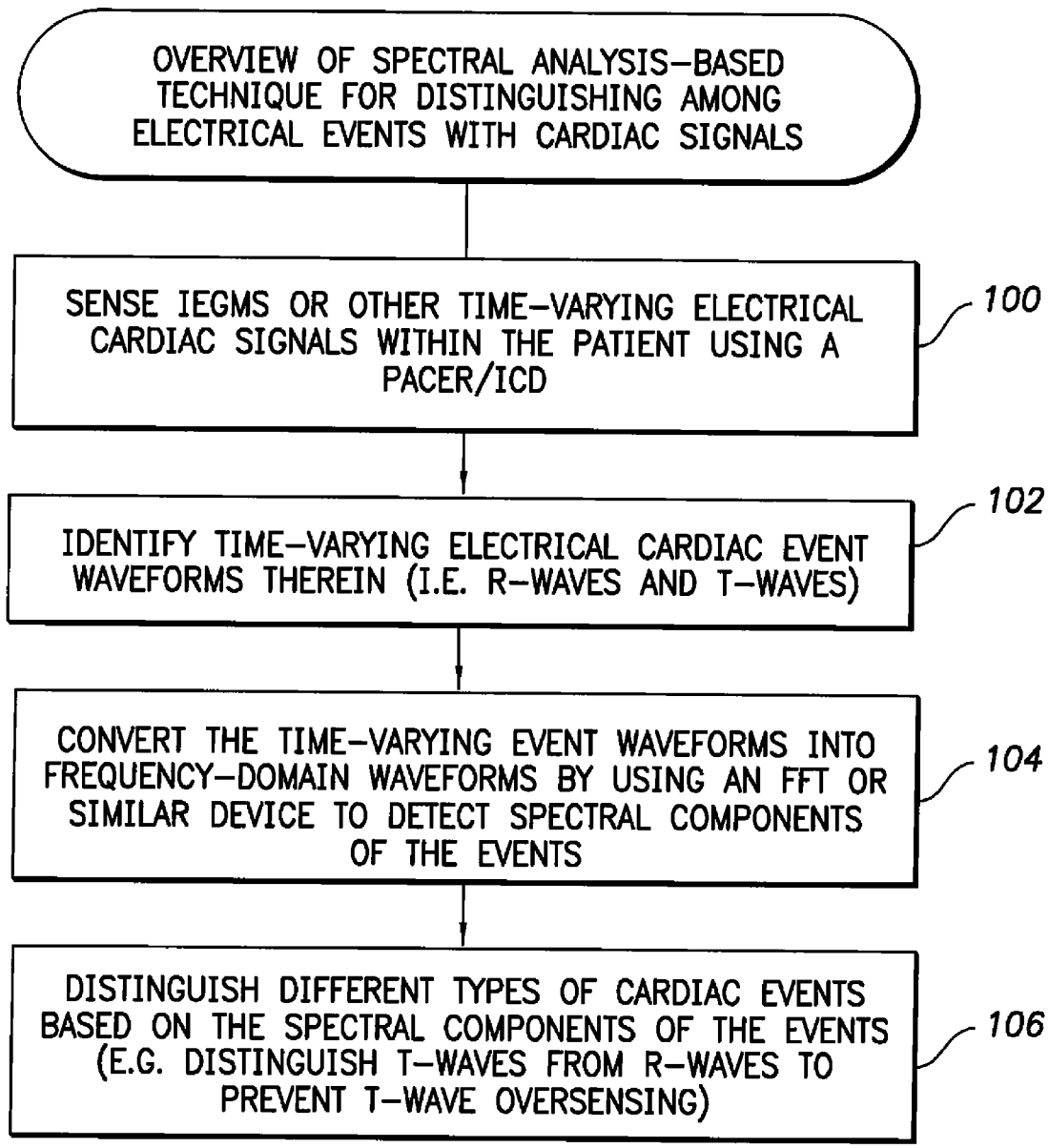
FIG. 3 provides an overview of spectral-based analysis techniques performed by the system of FIG. 2 for distinguishing R-waves and T-waves.

FIG. 3 provides an overview of the techniques of the invention for distinguishing cardiac events based on their spectral components. Briefly, beginning at step 100, the pacer/ICD senses electrical cardiac signals, such as IEGM signals, using one or more leads implanted within the patient. Otherwise conventional techniques may be used for converting voltage signals sensed using the various leads into IEGM or similar signals. At step 102, the pacer/ICD identifies time-varying electrical cardiac event waveforms therein (i.e. R-waves and T-waves.) Again, conventional techniques may be used, such as by detecting portions of the signal that exceed some event detection threshold specified by a programmable sensitivity value. At step 104, the pacer/ICD converts the time-varying event waveforms into frequency-domain waveforms by using an FFT or similar device to detect spectral components of the events. At step, 106, the pacer/ICD then distinguishes different types of cardiac events based on the spectral components of the events (to, e.g., distinguish R-waves from T-waves to prevent T-wave oversensing.)

Figure 1:
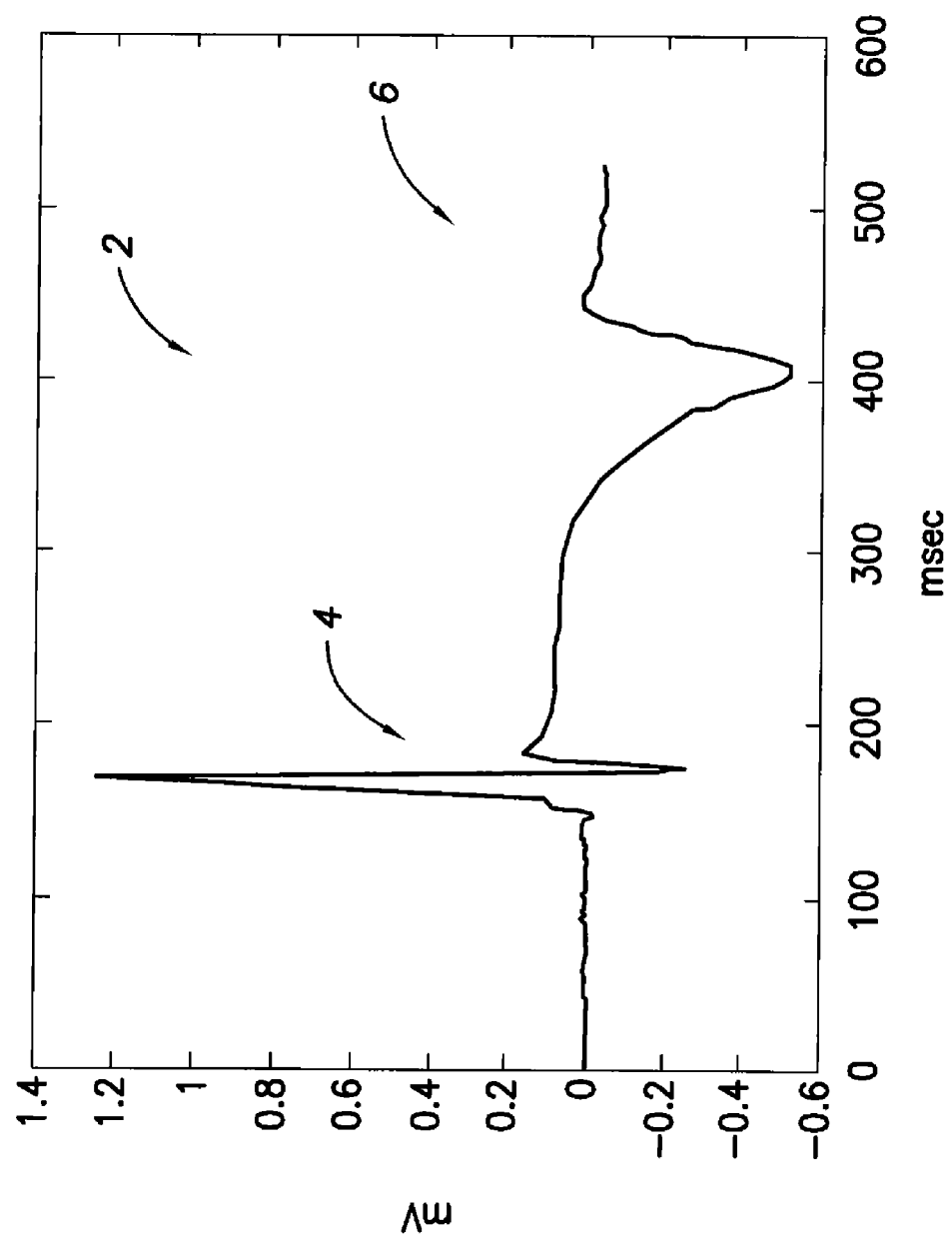
FIG. 1 is a graph illustrating a cardiac signal, particularly identifying R-waves and T-waves therein.
Figure 4:
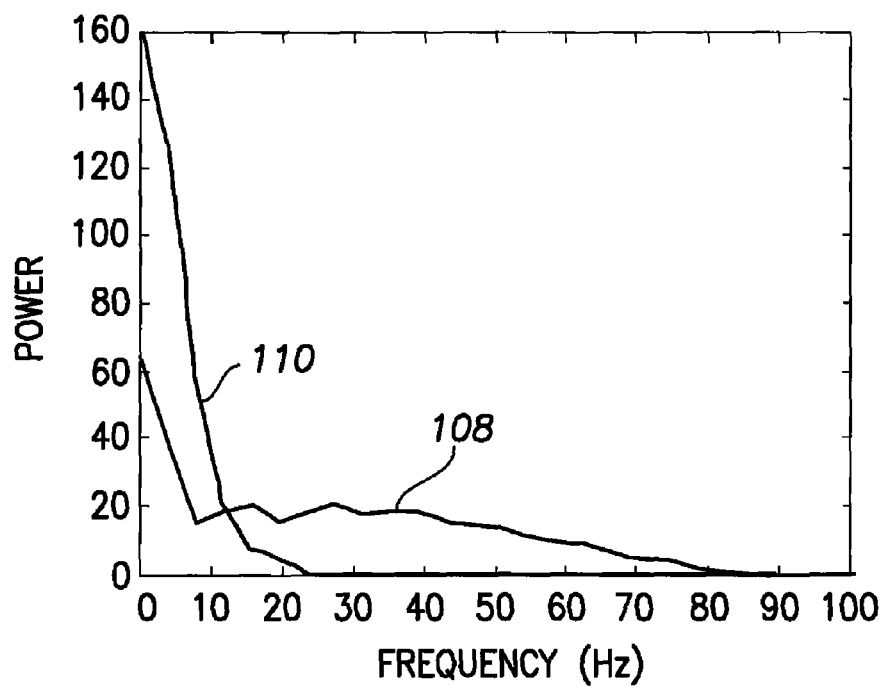
FIG. 4 is a graph illustrating the power spectrum for exemplary R-waves and T-waves for use in distinguishing R-waves from T-waves in accordance with the technique of FIG. 3, and particularly illustrating the minimal power components of T-waves beyond 25 Hz.

FIG. 4 illustrates the spectral components of exemplary R-waves and T-waves, i.e. the figure illustrates the frequency-domain decomposition of time-varying R-waves and T-waves, such as those illustrated in FIG. 1. A first curve 108 represents the spectral components of the R-wave; whereas a second curve 110 represents the spectral components of the T-wave. Frequencies of those components are represented along the X-axis of the graph. The amount of power at each frequency (i.e. the strength of the signal at each frequency) is represented along the Y-axis, in arbitrary power units. As can be seen, the R-wave exhibits considerable power up to 60 Hz and beyond. The T-wave, however, has little or no power beyond 25 Hz. As such, an analysis of the spectral components of ventricular events can be used to distinguish R-waves from T-waves. Various exemplary techniques are discussed above that exploit different portions of the frequency spectrum.

Figure 5:
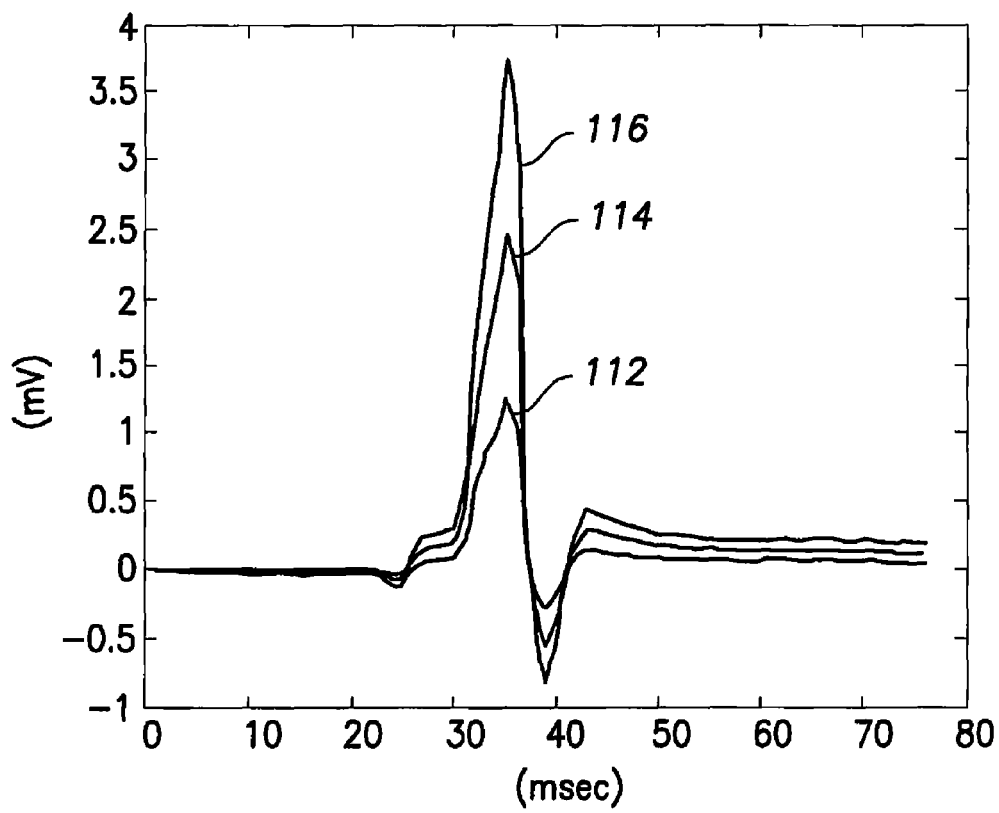
FIG. 5 is a graph illustrating exemplary R-waves of differing amplitudes for analysis by the technique of FIG. 3.
Figure 6:
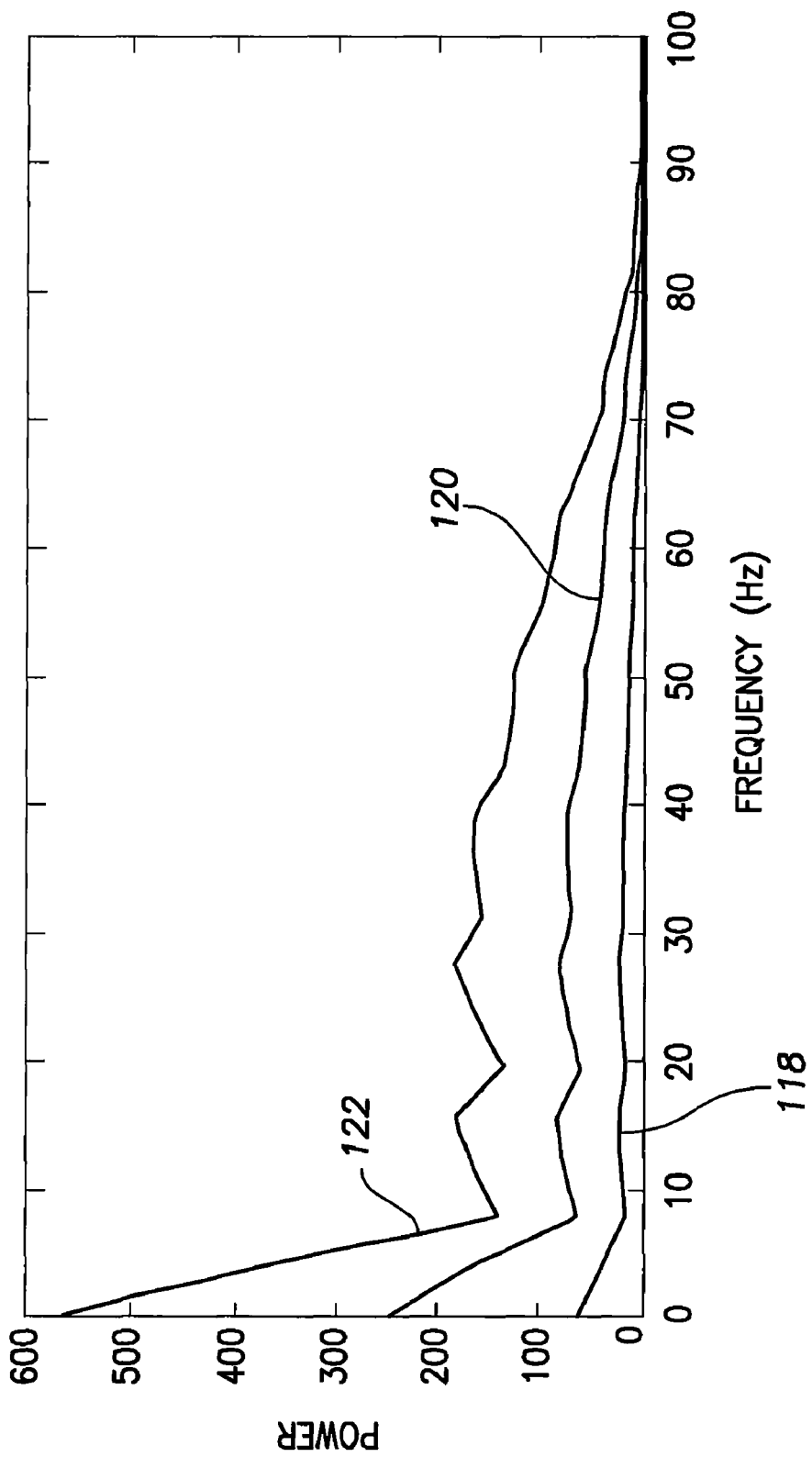
FIG. 6 is a graph illustrating power spectrums for the exemplary R-waves of FIG. 5, and particularly illustrating the insensitivity of R-wave amplitude on spectral analysis.
Figure 7:
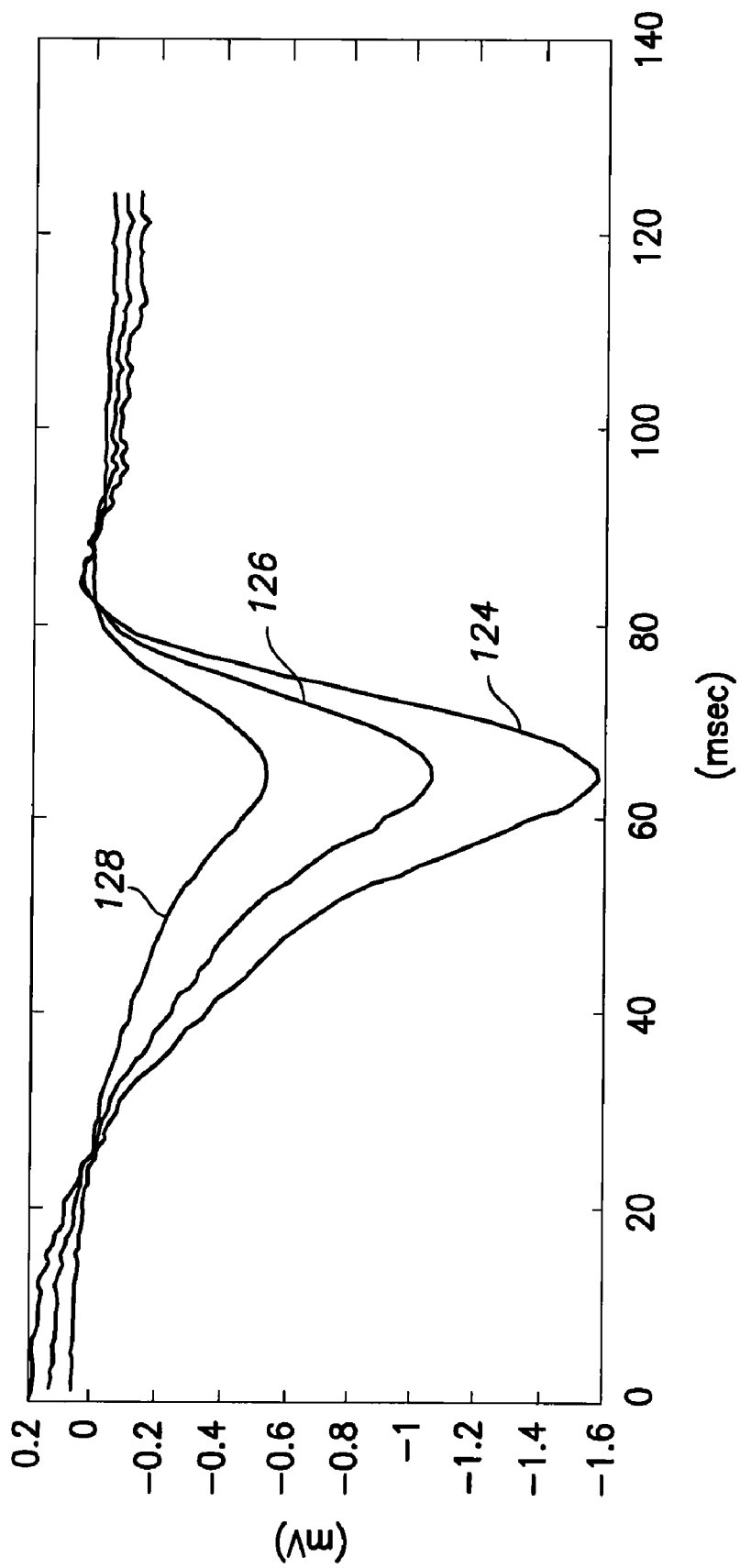
FIG. 7 is a graph illustrating exemplary T-waves of differing amplitudes for analysis by the technique of FIG. 3.
Figure 8:
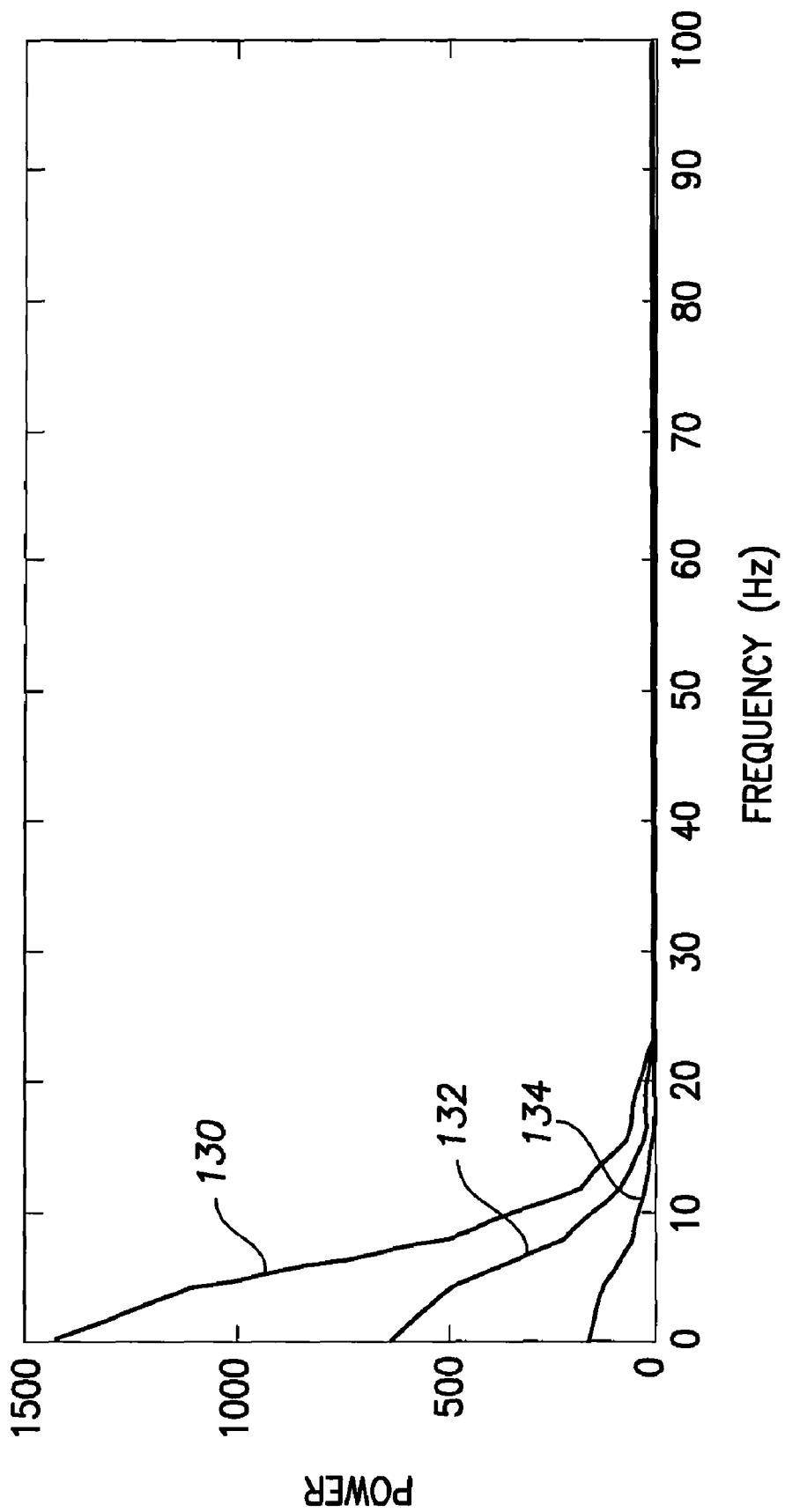
FIG. 8 is a graph illustrating power spectrums for the exemplary T-waves of FIG. 7, and particularly illustrating the insensitivity of T-wave amplitude on spectral analysis.

The amplitudes or sizes of R-waves and T-waves within an IEGM can be affected by a variety of factors within the patient, such as the use of medications, the occurrence of cardiac ischemia, myocardial infarctions, congestive heart failure, or other factors. Moreover, as explained above in the Background section, even the relative amplitudes of R-waves and T-waves, i.e. the size of the T-wave relative to the size of the R-wave within a given heartbeat, can vary within the patient. Advantageously, however, the spectral decomposition of the R-waves and T-waves is substantially unaffected by amplitude. This is illustrated within FIGS. 5-8. Briefly, FIG. 5 illustrates a set of three R-waves of differing amplitudes 112, 114, and 116 and FIG. 6 illustrates the spectral decomposition of those R-waves, as curves 118, 120 and 122, respectively. As can be seen, the spectra curves of FIG. 6 have substantially the same shape; the curves differ only in magnitude. Hence, the relative percentages of the amounts of power within certain frequency bands (or at certain individual frequencies) remains unchanged despite changes in R-wave amplitude. And, in particular, regardless of amplitude, the power spectrum of each R-wave still exhibits substantial portions up to 60 Hz and beyond. Likewise, FIG. 7 illustrates a set of three T-waves of differing amplitudes 124, 126, and 128 and FIG. 8 illustrates the spectral decomposition of those R-waves, as curves 130, 132 and 134, respectively. As can be seen, the power curves of FIG. 8 have substantially the same shape and differ only in magnitude. In particular, regardless of amplitude, the power spectrum of each T-wave still exhibits little or no power beyond 25 Hz. As such, variations in the amplitude of R-waves and T-waves do not affect the capability of the pacer/ICD to distinguish one from the other based on their spectral decomposition.

Note also that changes in heart rate can affect the shape of the R-waves and the T-waves, and hence can also affect their spectral decomposition. However, the difference is not sufficient to prevent the spectral decomposition from being reliably used to distinguish R-waves from T-waves. Also, medical conditions such as cardiac ischemia, myocardial infarctions, etc., can also affect the shape of the R-waves and the T-waves and their spectral decomposition. In at least some cases, ischemia can potentially change the morphology enough to significantly shift the spectral features. Hence, the threshold that is used to distinguish R-waves from T-waves is preferably set so as to include R-wave during ischemia. That is, the threshold is set to distinguish R-waves (whether normal or ischemic) from T-waves (whether normal or ischemic.)

Still further, although examples described herein primarily involve the discrimination of R-waves and T-waves, the general technique of FIG. 3 can be used to distinguish other types of cardiac events, such as to distinguish P-waves from R-waves, or to distinguish atrial evoked responses (AERs) from ventricular evoked responses (VERs), if needed, or to distinguish different types of Fib-waves. Hence, the invention should not be construed as being limited to the discrimination of only R-waves and T-waves. Spectral-based techniques for detecting and distinguishing ventricular arrhythmias are discussed below. Spectral-based techniques for detecting and distinguishing atrial arrhythmias are discussed in U.S. patent application Ser. No. 11/841,243, cited above which is incorporated by reference herein in its entirety.

FFT-Based Discrimination Procedures

Figure 9:
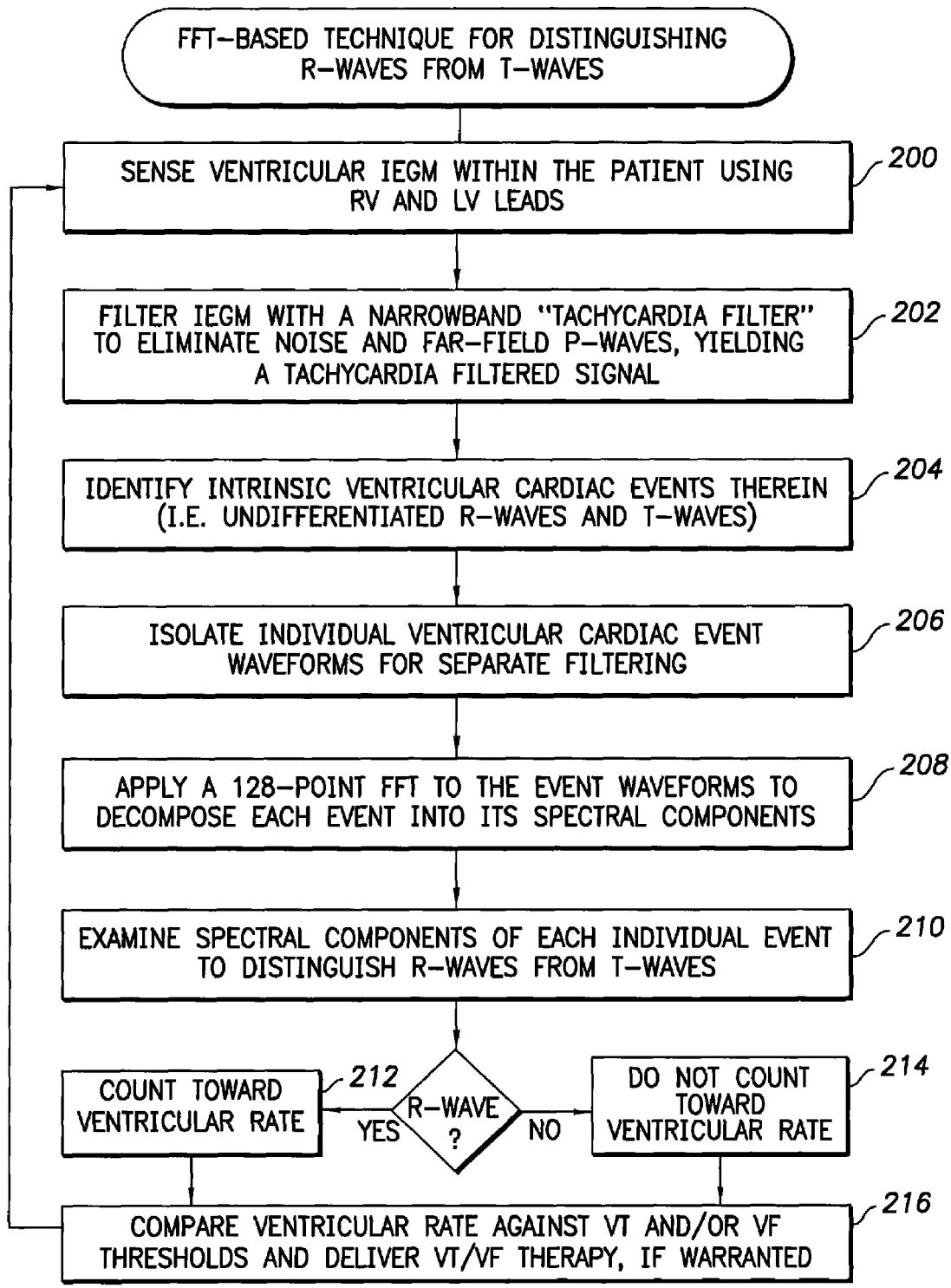
FIG. 9 illustrates an illustrative example of a spectral technique for distinguishing R-waves from T-waves, in accordance with the general technique of FIG. 3, wherein a 128 point FFT is exploited.

FIG. 9 illustrates an FFT-based technique for distinguishing R-waves from T-waves in accordance with the general method set forth in FIG. 3. Beginning at step 200, the pacer/ICD senses ventricular IEGM within the patient using RV and LV leads and, at step 202, filters the IEGM with a narrowband "tachycardia filter" to eliminate noise and far-field P-waves, yielding a tachycardia filtered signal. By a "tachycardia filter," it is meant a filter configured to pass cardiac signals appropriate for the detection of tachycardia (particularly relatively high rate ventricular events) while filtering out substantially all other cardiac events. An otherwise conventional tachycardia filter can be employed. For further information regarding tachycardia filters and other filters for use in pacer/ICDs see, e.g., U.S. patent application Ser. No. 11/776,266, of Bharmi-Sarai et al., filed Jul. 11, 2007, entitled "Systems and Methods for Employing Multiple Filters to Detect T-Wave Oversensing and To Improve Tachyarrhythmia Detection within an Implantable Medical Device."

At step 204, the pacer/ICD identifies intrinsic ventricular cardiac events therein (i.e. undifferentiated R-waves and T-waves) using any suitable technique. Typically, the amplitude of the tachycardia-filtered signal is compared against a detection threshold set based on a programmable sensitivity value. By using a tachycardia-filtered signal derived from ventricular IEGM signals, it can be substantially assumed that any event detected therein is a ventricular event of some type, such that the pacer/ICD need not further distinguish between atrial events and ventricular events. Though, in other implementations, the principles of the invention can be applied to distinguish between atrial and ventricular events, where appropriate.

Note also that, if the ventricles are being paced by the pacer/ICD, then R-waves are no longer present within the IEGM. Rather, a VER appears within the IEGM, which is representative of the depolarization of the ventricular myocardium due to the application of an artificial pacing pulse. The shape of the VER typically differs from that of the R-wave. For the purposes of the technique of FIG. 9, it is assumed that ventricular pacing is not being performed, and hence VERs do not appear within the tachycardia-filtered signal. Nevertheless, if ventricular pacing is being performed, the techniques of the invention can be readily extended to distinguishing R-waves from VERs, if necessary. Moreover, as will be explained further with reference to FIGS. 12 and 13, the FFT-based discrimination technique is preferably employed only at the high ventricular rates associated with VT or VF. At those rates, ventricular pacing is typically not employed and hence the pacer/ICD need not distinguish between R-waves and VERs. Hence, at those high rates, it need only distinguish between R-waves and T-waves so as to detect and eliminate T-wave oversensing.

At step 206, the pacer/ICD isolates individual ventricular cardiac event waveforms for separate filtering. That is, the pacer/ICD determines the beginning and end points of the ventricular events so that those portions of the tachycardia-filtered signal that correspond to the event itself can then be applied to the FFT. Otherwise conventional techniques may be applied for identifying the boundaries of ventricular events within an IEGM or other electrical cardiac signal. In one example, the pacer/ICD simply identifies the boundaries of the ventricular event as being the first and last points where the amplitude of the cardiac signal exceeds the aforementioned event detection threshold. Other event boundary detection techniques may be exploited, where appropriate. See, e.g., the event boundary detection techniques described in: U.S. patent application Ser. No. 11/043,612, of Kil et al., filed Jan. 25, 2005, entitled "System and Method for Distinguishing among Cardiac Ischemia, Hypoglycemia and Hyperglycemia using an Implantable Medical Device"; U.S. Patent Application Serial Number 2004/0077962 of Kroll, published Apr. 22, 2004, entitled "System and Method for Monitoring Blood Glucose Levels Using an Implantable Medical Device"; and U.S. Pat. No. 6,650,931 to McClure, et al., entitled "System and Method of Automatically Determining the Onsets and Ends Of Cardiac Events and Far-Field Signals."

At step 208, the pacer/ICD applies, in this example, a 128-point FFT to the event waveforms isolated at step 206 to decompose each event into its spectral components, i.e. to convert the event waveform from the time-domain to the frequency-domain so as to determine the power spectrum for each event. Other FFTs can alternatively be used. FIG. 4, discussed above, illustrates exemplary frequency-domain waveforms representative of the power spectrum of ventricular events. An otherwise conventional FFT may be employed, either implemented in software using the microprocessor of the device or implemented as a separate dedicated hardware device, such as an application specific integrated circuit (ASIC). Given that the FFT need not be used at all times by the pacer/ICD and can instead be activated, e.g., only during episodes of suspected VT/VF, it is typically feasible to implement the FFT in software without unduly consuming processing resources. Note also that the FFT, when not being used for event discrimination, can be exploited for other purposes as well, such as apnea detection.

At step 210, the pacer/ICD examines the spectral components of each individual event to distinguish R-waves from T-waves. Various exemplary techniques will be described below with reference to FIG. 10. If the pacer/ICD determines that the ventricular event is an R-wave, then it is counted toward the ventricular rate, at step 212, otherwise it is not counted toward the ventricular rate, at step 214. In either case, the pacer/ICD then compares the ventricular rate against VT and/or VF thresholds and delivers VT/VF therapy if warranted. As will be explained below, in some implementations, the FFT is not activated until the ventricular rate exceeds a threshold indicative of possible VT/VF. In other words, steps 206-210 of FIG. 9 are only performed if a possible VT/VF had already been detected.

Figure 10:
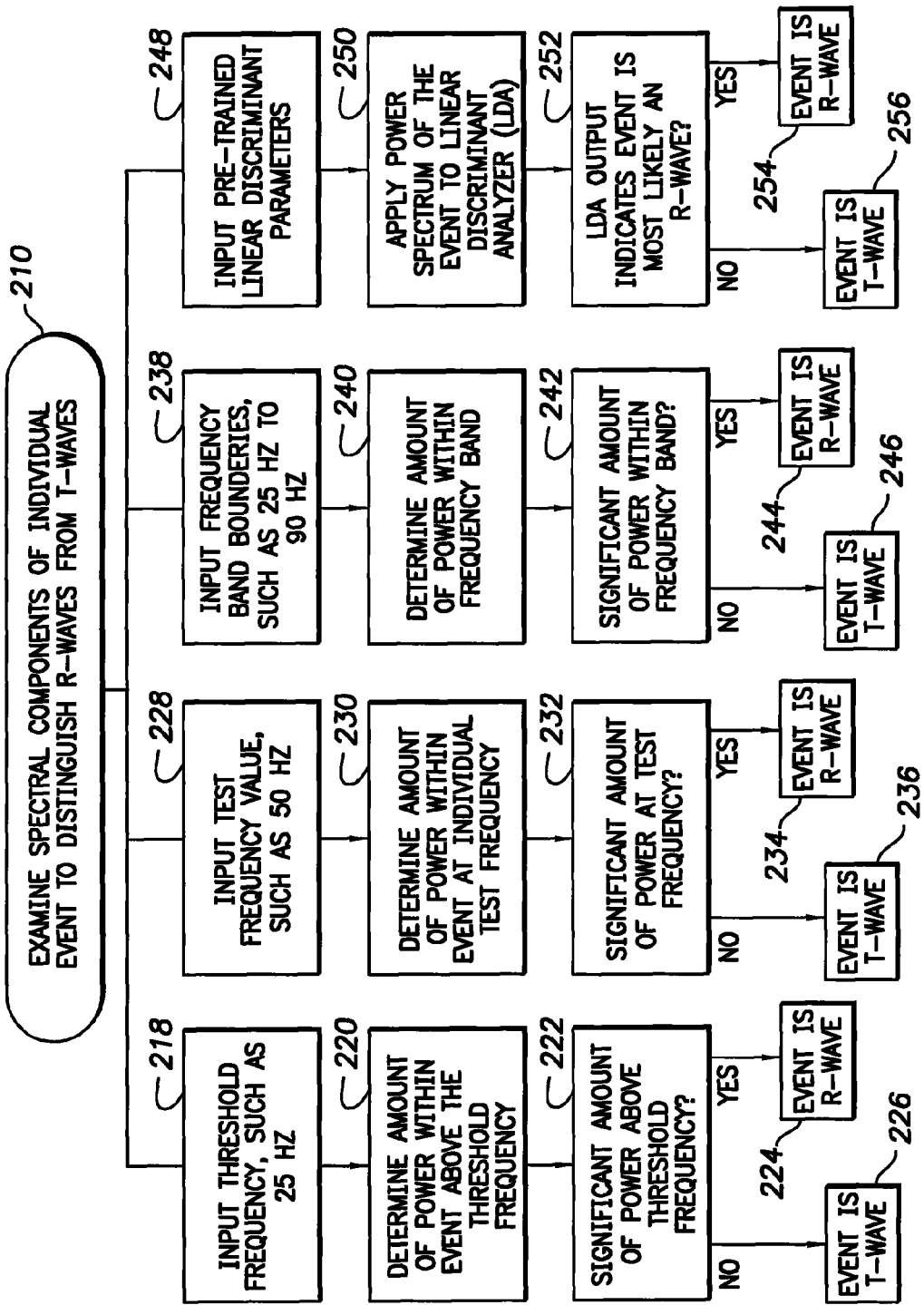
FIG. 10 particularly illustrates techniques for examining spectral components of individual ventricular events for use with the technique of FIG. 9.

Turning now to FIG. 10, various techniques for use at step 210 of FIG. 9 for examining spectral components of each individual ventricular event to distinguish R-waves from T-waves will now be described. The various techniques of FIG. 10 may be exploited individually or, in some cases, in parallel.

In a first exemplary technique, R-waves and T-waves are distinguished by comparing the amount of power found within the ventricular event above a threshold frequency. Beginning at step 218, the pacer/ICD inputs a threshold frequency, such as 25 Hz, from memory. The threshold frequency is a predetermined value above which T-waves exhibit little or no power. In some embodiments, the threshold value is preset by the device manufacturer. In other embodiments, the value is programmable or adjustable by the physician using an external programmer. In still other embodiments, to be described below with reference to FIG. 11, the pacer/ICD determines the value in advance based on the power characteristics of R-waves and T-waves within the particular patient in which the device is implanted. In any case, at step 220, the pacer/ICD determines the total amount of power within the event above the threshold frequency. That is, the pacer/ICD calculates the area under the frequency-domain waveform output by the FFT for the event at frequencies above the threshold frequency. Otherwise conventional numerical techniques for summing or integrating the area under the waveform may be exploited. At step 222, the pacer/ICD then determines whether there is a significant amount of power within the event above threshold frequency. If there is a significant amount of power above the threshold frequency, the event is determined to be an R-wave, step 224. Otherwise, it is determined to be a T-wave (or other non-R-wave event), at step 226. For example, at step 222, the pacer/ICD may compare the power value calculated at step 220 against a minimum power threshold retrieved from memory. As with the frequency threshold value, the power threshold value can be preset within the device, programmed by a physician, or determined by the device itself. Given that T-waves typically exhibit little or no power about 25 Hz, the power threshold value for use at step 222 can typically be quite small.

In a second exemplary technique, R-waves and T-waves are distinguished by comparing the amount of power found at a particular test frequency, rather than above some threshold frequency. Beginning at step 228, the pacer/ICD inputs an individual test frequency value, such as 50 Hz, from memory. The threshold frequency is a predetermined value at which T-waves exhibit little or no power. At step 230, the pacer/ICD determines the amount of power within the event at the test frequency. That is, the pacer/ICD merely reads out the amplitude of the frequency domain waveform for the event at the test frequency. At step 232, the pacer/ICD then determines whether there is a significant amount of power within the event at the test frequency. If so, the event is determined to be an R-wave, step 234. Otherwise, it is determined to be a T-wave (or other non-R-wave event), at step 236. Again, a pre-determined minimum power threshold value may be retrieved from memory. Both the test frequency and the power threshold value can be preset within the device, programmed by a physician, or determined by the device itself. Given that T-waves typically exhibit no power at all at 50 Hz, the power threshold value for use at step 232 can be set near zero.

In a third exemplary technique, R-waves and T-waves are distinguished by comparing the amount of power found within a frequency band. Beginning at step 238, the pacer/ICD inputs upper and lower boundaries for a test frequency band, such as 25 Hz and 90 Hz, from memory. The frequency band is a predetermined range of values within which T-waves exhibit little or no power. At step 240, the pacer/ICD determines the amount of power for the event within the test frequency band. Again, otherwise conventional summation or integration techniques may be employed. At step 242, the pacer/ICD then determines whether there is a significant amount of power within the frequency band. If so, the event is determined to be an R-wave, step 244. Otherwise, it is determined to be a T-wave (or other non-R-wave event), at step 246. As before, a pre-determined minimum power threshold value may be retrieved from memory. Both the frequency band boundary values and the power threshold value can be preset within the device, programmed by a physician, or determined by the device itself. Given that T-waves typically exhibit little or no power between 25 and 90 Hz, the power threshold value for use at step 242 can be quite small.

In a fourth exemplary technique, R-waves and T-waves are distinguished by employing a linear discriminate analyzer (LDA). Beginning at step 248, the pacer/ICD inputs LDA parameters from memory, such as weight factors, for an LDA pre-trained to distinguish R-waves from T-waves within the patient. At step 250, the pacer/ICD applies the power spectrum for the event to the LDA, which outputs a signal indicating whether the event is an R-wave or a T-wave (or other non-R-wave event). Otherwise conventional LDA techniques may be exploited. In some examples, the entire power spectrum for the event is applied to the LDA. In other examples, only a portion of the power spectrum might be applied, such as only that portion within a predetermined frequency band. In any case, if, at step 252, the LDA output indicates that the event is most likely an R-wave, then, the event is deemed to be an R-wave, at step 254. Otherwise, the event is deemed to be a T-wave, step 256. The LDA parameters input at step 248 are preferably determined by the device itself for use with the particular patient in which the device is implanted.

Hence, FIG. 10 illustrates various exemplary techniques for distinguishing R-waves from T-waves based on power spectra derived from an FFT. Other techniques may additionally, or alternatively, be exploited. Typically, it is sufficient for the pacer/ICD to be equipped to exploit only one of these techniques. However, a pacer/ICD may be equipped to exploit multiple techniques and to then make the final determination of whether the event is an R-wave or a T-wave based on the results of several techniques. In an implementation where the pacer/ICD is to distinguish among a greater variety of events, such as among P-waves, R-waves and T-waves, the techniques of FIG. 10 may be modified as needed to accommodate the greater variety of events. For example, multiple test frequencies may be specified or multiple power threshold values may be specified, by which the device can distinguish among the various events. An LDA may be provided that is equipped to distinguish among a greater number of possible events as well.

Parameters Optimization Procedures

Figure 11:
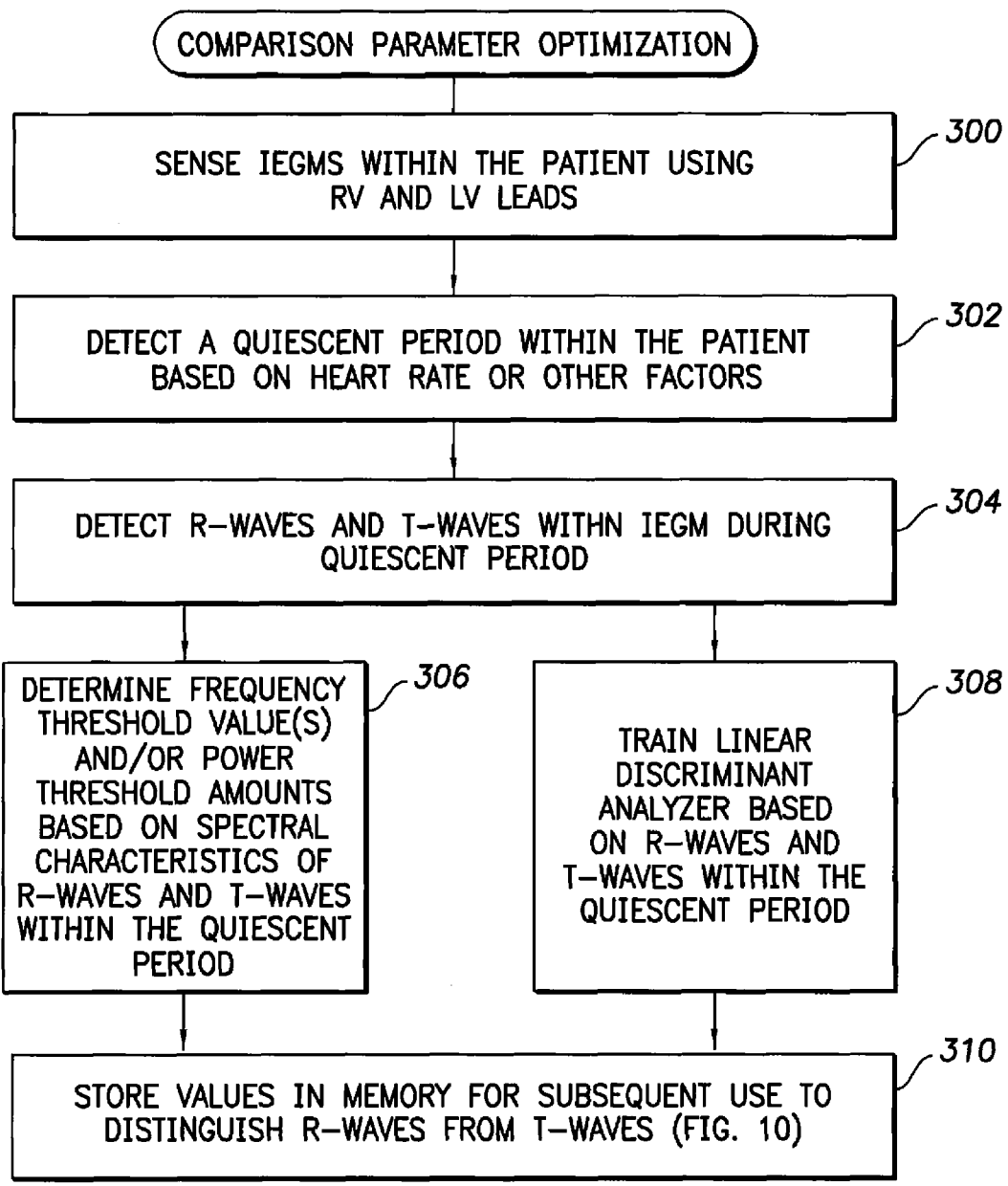
FIG. 11 particularly illustrates techniques for determining suitable comparison values during an initial quiescent period for later use with the technique of FIG. 9.

FIG. 11 summarized techniques for determining, adjusting or optimizing any or all of the comparison parameters used in FIG. 10. The techniques of FIG. 11 may be, for example, performed following device implant to set initial values for the comparison parameters within the patient and may be performed periodically thereafter to adjust or update the values to account for changes to the morphology of R-waves and T-waves in the patient caused by prescription medications, progression of heart disease, episodes of ischemia, etc. Beginning at step 300, the pacer/ICD senses IEGMs within the patient and, at step 302, detects a quiescent period within the patient based on, at least, the heart rate of the patient. That is the pacer/ICD identifies a period of time when the patient is at rest so that R-waves and T-waves are expected to have nominal morphologies. Patient posture may also be exploited to identify the quiescent period. At step 304, the pacer/ICD detects R-waves and T-waves during the quiescent period.

At step 306, the pacer/ICD determines frequency threshold values(s) and/or power threshold amounts based on spectral characteristics of R-waves and T-waves within the quiescent period. That is, the pacer/ICD distinguishes R-waves from T-waves using otherwise conventional techniques (which may be processor intensive). The pacer/ICD also applies the R-waves and T-waves to the FFT to decompose the events into their power spectra. The pacer/ICD then determines optimal values for the various comparison threshold values for use in the technique of FIG. 10 based on the power spectra of the events. For example, if a fixed test frequency is to be exploited, the pacer/ICD identifies the optimal test frequency (or at least a preferred test frequency) to be used to distinguish R-waves from T-waves within the patient. Otherwise conventional adaptive techniques may be exploited to this end.

If an LDA is to be exploited, the pacer/ICD, at step 308, trains the LDA based on the R-waves and T-waves detected within the quiescent period. That is, the pacer/ICD again distinguishes between R-waves and T-waves using otherwise conventional detecting techniques (which may be processor intensive). Then, the power spectra of each individual ventricular event is determined using the FFT and then applied to the LDA along with an indication of whether the event is an R-wave or a T-wave, so as to train the LDA to recognize R-waves and T-waves. Any of a variety of otherwise conventional R-wave/T-wave detection techniques can be used at steps 306 and 308 to initially detect and distinguish R-waves and T-waves, such as techniques that examine the morphology of the individual events. As such techniques may be processor intensive, it is preferred that the techniques are used only during quiescent periods wherein there are no significant resource conflicts. Once the various comparison values have been obtained or the LDA has been trained, the more efficient FFT-based techniques of the invention can then be exploited to distinguish R-waves from T-waves, particularly during VT/VF. In some examples, the LDA is trained at different rates during the quiescent period so that the LDA values are not based only on low rates. This can be achieved by atrial pacing at different rates.

R-Wave/T-Wave Discrimination Activation Procedures

Figure 12:
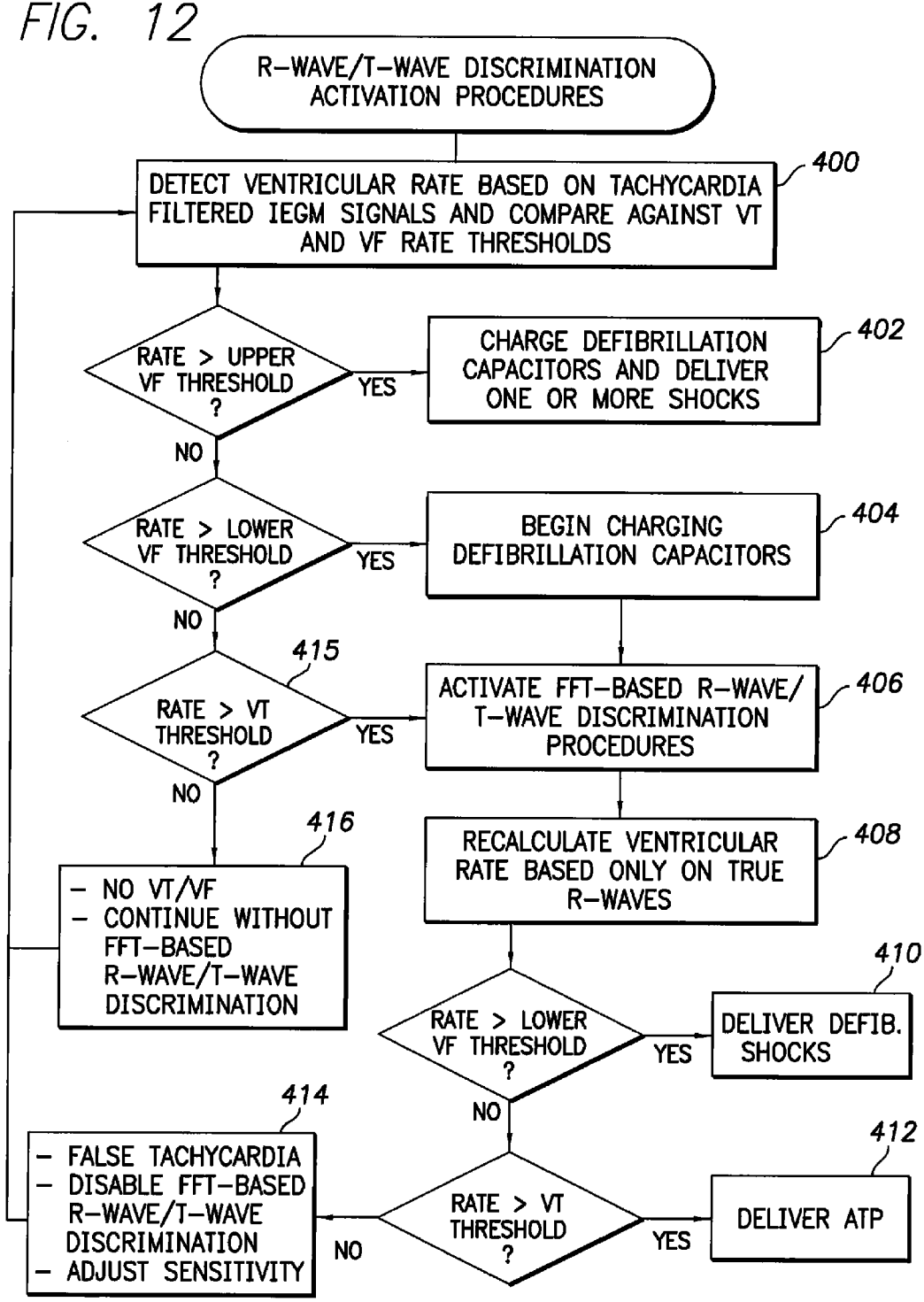
FIG. 12 particularly illustrates techniques for activating the R-wave/T-waves discrimination technique of FIG. 9 based on ventricular rate.
Figure 13:
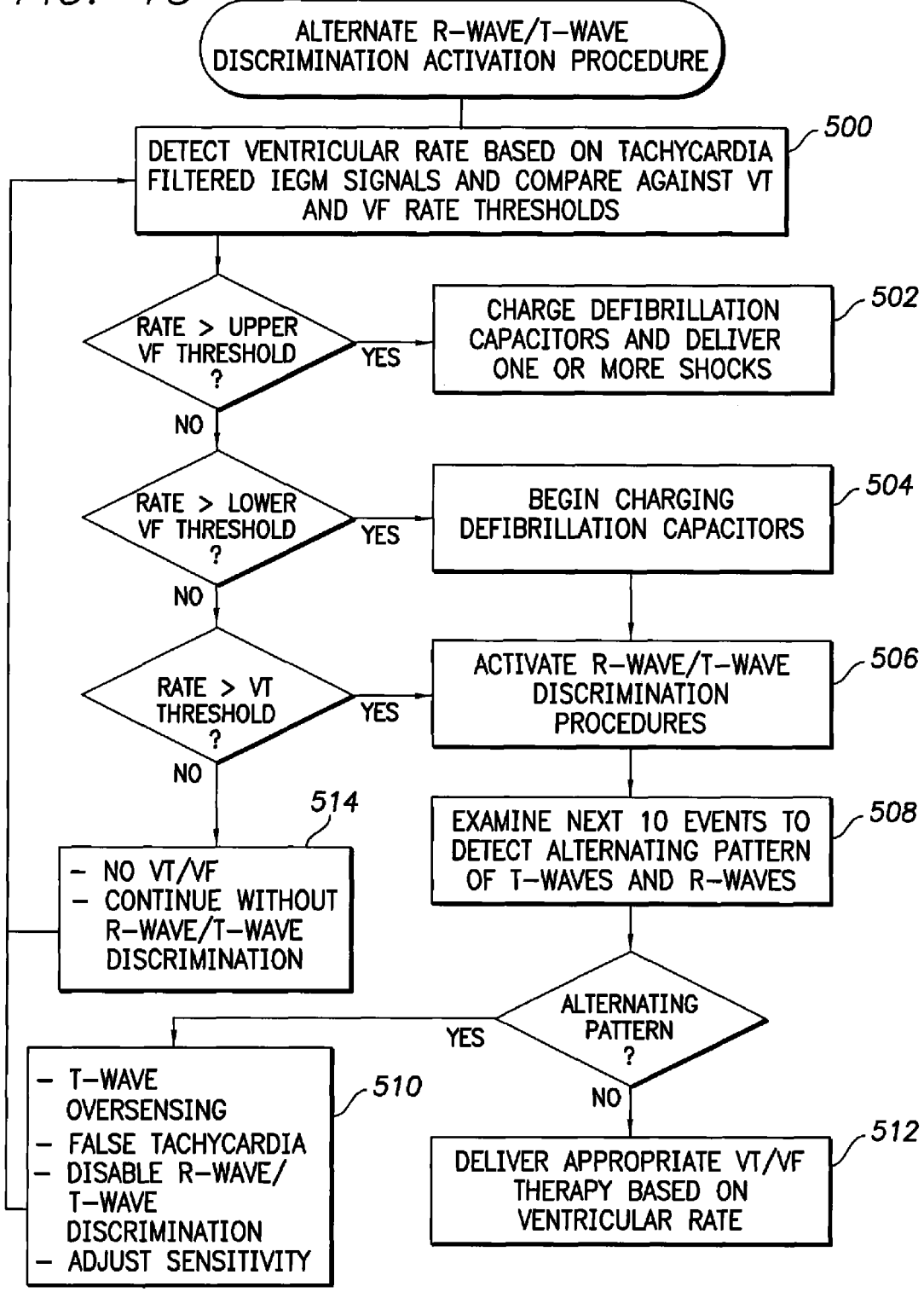
FIG. 13 illustrates an alternate technique to that of FIG. 12 wherein T-wave oversensing is detected based on alternating sequences of R-waves and T-waves.

Turning now to FIGS. 12-13, various techniques for triggering FFT-based R-wave/T-wave discrimination will now be described, along with techniques for detecting T-wave oversensing and for triggering delivery of VT/VF therapy. With the technique of FIG. 12, the FFT-based discrimination procedures are only activated if VT/VF is suspected. Beginning at step 400, the pacer/ICD detects a ventricular rate within the patient based on tachycardia-filtered IEGM signal and compares the rate against various predetermined VT and VF thresholds. That is, the pacer/ICD assumes all events detected within the tachycardia-filtered signals are R-waves and calculates the ventricular rate based on that assumption. If the rate is found to exceed an upper VF threshold set, e.g., to 220 bpm, then step 402 is performed, where the pacer/ICD charges its defibrillation capacitors and delivers one or more defibrillation shocks. That is, no FFT-based analysis if performed. The high rate is presumed to be indicative of a true VF, regardless of whether some T-wave oversensing might be occurring, and so shocks are delivered as soon as possible. Typically, it can take some time before the capacitors are sufficiently charged to deliver the shocks. During this period of time, the pacer/ICD continues to monitor the ventricular rate. Although not shown in FIG. 12, if the rate drops below the upper VF threshold before the capacitors are fully charged, the pacer/ICD defers delivering the shock pending confirmation of VF in accordance with the remaining steps of FIG. 12.

Assuming that the ventricular rate is not above the upper VF threshold, the rate is compared against a lower VF threshold set, e.g., to 167 bpm. If the rate exceeds the lower VF threshold, then, at step 404, the pacer/ICD also begins to (or continues to) charge the defibrillation capacitors. While the capacitors are being charged, the pacer/ICD, at step 406, activates the FFT-based R-wave/T-wave discrimination procedures of FIG. 9 to distinguish R-waves from T-waves and, at step 408, recalculates the ventricular rate based only on true R-waves. If the rate still exceeds the lower VF threshold, the pacer/ICD delivers defibrillation shocks at step 410, once the capacitors are charged. Particularly effective techniques for generating and delivering defibrillation shocks are described in U.S. Pat. No. 6,415,179 to Pendekanti, et al., entitled "Method and Apparatus for Improving the Probability of Success of Defibrillation Shocks" and in U.S. Pat. No. 5,749,901 to Bush, et al., entitled "Method and Apparatus for Delivering Defibrillation Shocks with Improved Effectiveness." See, also, U.S. Pat. No. 6,772,007 to Kroll, entitled "System and Method of Generating a Low-Pain Multi-Step Defibrillation Waveform for Use in an Implantable Cardioverter/Defibrillator (ICD)."

However, if the ventricular rate calculated at step 408 is merely above a still lower VT threshold set to, e.g., 120 bpm, then ATP is instead delivered at step 412. ATP is discussed in, e.g., U.S. Pat. No. 6,907,286 to Kroll, et al., entitled "Anti-tachycardia Pacing Methods and Devices". If the recalculated ventricular rate is below even the VT threshold, then the pacer/ICD determines that the initial high ventricular rate was due to T-waves oversensing and disables the FFT-based R-wave/T-wave discrimination procedures of FIG. 9, at step 414. Also, at step 414, the pacer/ICD can take steps to adjust the sensitivity with which ventricular events are detected in an attempt to prevent further T-waves oversensing.

Note that, if the ventricular rate initially detected at step 400 was found to be greater than the VT threshold, at decision step 415, but not greater than the lower VF threshold, then the FFT-based R-wave/T-wave discrimination procedures are activated at step 408, without also pre-charging the defibrillation capacitors. That is, in this case, the ventricular rate initially detected at step 400 did not reach the VF zone and hence VF is not presumed and so the capacitors are not charged. The FFT-based R-wave/T-wave discrimination procedures are nevertheless activated to address possible T-wave oversensing before ATP is triggered.

Also, if the ventricular rate initially detected at step 400 did not exceed any of the VT/VF thresholds, then no VT/VF is detected, at step 416, and processing continues without the FFT-based R-wave/T-wave discrimination procedures.

FIG. 13 illustrates an alternative implementation for triggering R-wave/T-wave discrimination, which also provides an alternating pattern-based procedure for detecting T-wave oversensing. Many of the steps of FIG. 13 are similar to those of FIG. 12 and will not be described in detail again. At step 500, the pacer/ICD detects a ventricular rate and then compares the rate against various predetermined VT and VF thresholds. If the rate is found to exceed the upper VF threshold, step 502 is performed where the pacer/ICD charges its defibrillation capacitors and delivers one or more defibrillation shocks. If the ventricular rate is between the upper and lower VF thresholds, steps 504 and 506 are performed wherein the pacer/ICD begins to charge the defibrillation capacitors and activates the FFT-based R-wave/T-wave discrimination procedures.

At step 508, the pacer/ICD then examines the next 10 events (or some other programmable number of events) to detect an alternating pattern of T-waves and R-waves. That is, the pacer/ICD uses the FFT to distinguish R-waves from T-waves. Then, the pacer/ICD examines the pattern of R-waves and T-waves to determine whether R-waves and T-waves are alternating consistently. If so, then significant T-wave oversensing is occurring and so the high ventricular rate was likely due to such oversensing and, at step 510, appropriate steps are taken to adjust the sensitivity of the tachycardia filter to prevent further T-wave oversensing. The FFT-based R-wave/T-wave discrimination procedures are also deactivated at step 510. If, instead, T-waves appear only occasionally or randomly within a sequence of R-waves, then no significant T-wave oversensing is occurring and, hence, the high ventricular rate originally detected was properly indicative of a true VT/VF and so appropriate VT/VF therapy is delivered at step 512. (Also, if the ventricular rate initially detected at step 500 did not exceed any of the VT/VF thresholds, then no VT/VF is detected, at step 514, and processing continues without the FFT-based R-wave/T-wave discrimination procedures.)

Hence, FIGS. 12 and 13 illustrated techniques for detecting VT and VF based on ventricular rate and activating the FFT accordingly. Therapy is delivered in response to a true VT/VF.

In the examples, VF is distinguished from VT based on the ventricular rate. More sophisticated VT/VF discrimination techniques may be employed as well. See, for example, U.S. Pat. No. 5,404,880 to Throne, entitled "Scatter Diagram Analysis System and Method for Discriminating Ventricular Tachyarrhythmias".

Thus, various techniques have been described for distinguishing R-waves from T-waves using an FFT or similar device and for delivering VT/VF therapy where appropriate. Note that, whereas the techniques are preferably employed in "real time" based on IEGM signals as they are sensed, the techniques can alternatively be employed based on previously recorded signals. For example, IEGM data may be collected over time then analyzed later to detect and distinguish R-waves and T-waves for the purpose of generating appropriate diagnostic data for physician review. Such delayed analysis techniques can be performed either using the implanted device itself or using an external data processing device based on data transmitted from the implanted device. Real time detection is preferred as it allows T-wave oversensing to be promptly detected so that therapy can be controlled, as needed.

For the sake of completeness, a detailed description of an exemplary pacer/ICD for performing these techniques will now be provided. However, principles of invention may be implemented within other pacer/ICD implementations or within other devices.

Exemplary Pacemaker/ICD

FIG. 14 provides a simplified block diagram of the pacer/ICD, which is a multi-chamber stimulation device capable of treating both fast and slow arrhythmias with stimulation therapy, including cardioversion, defibrillation, and pacing stimulation (as well as capable of detecting T-wave oversensing, detecting tachyarrhythmias, and delivering appropriate therapy.) To provide atrial chamber pacing stimulation and sensing, pacer/ICD 10 is shown in electrical communication with a heart 612 by way of a left atrial lead 620 having an atrial tip electrode 622 and an atrial ring electrode 623 implanted in the atrial appendage. Pacer/ICD 10 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 624 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 624 is designed to receive atrial and ventricular cardiac signals and to deliver left ventricular pacing therapy using at least a left ventricular tip electrode 626, left atrial pacing therapy using at least a left atrial ring electrode 627, and shocking therapy using at least a left atrial coil electrode 628. With this configuration, biventricular pacing can be performed. Although only three leads are shown in FIG. 14, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 15:
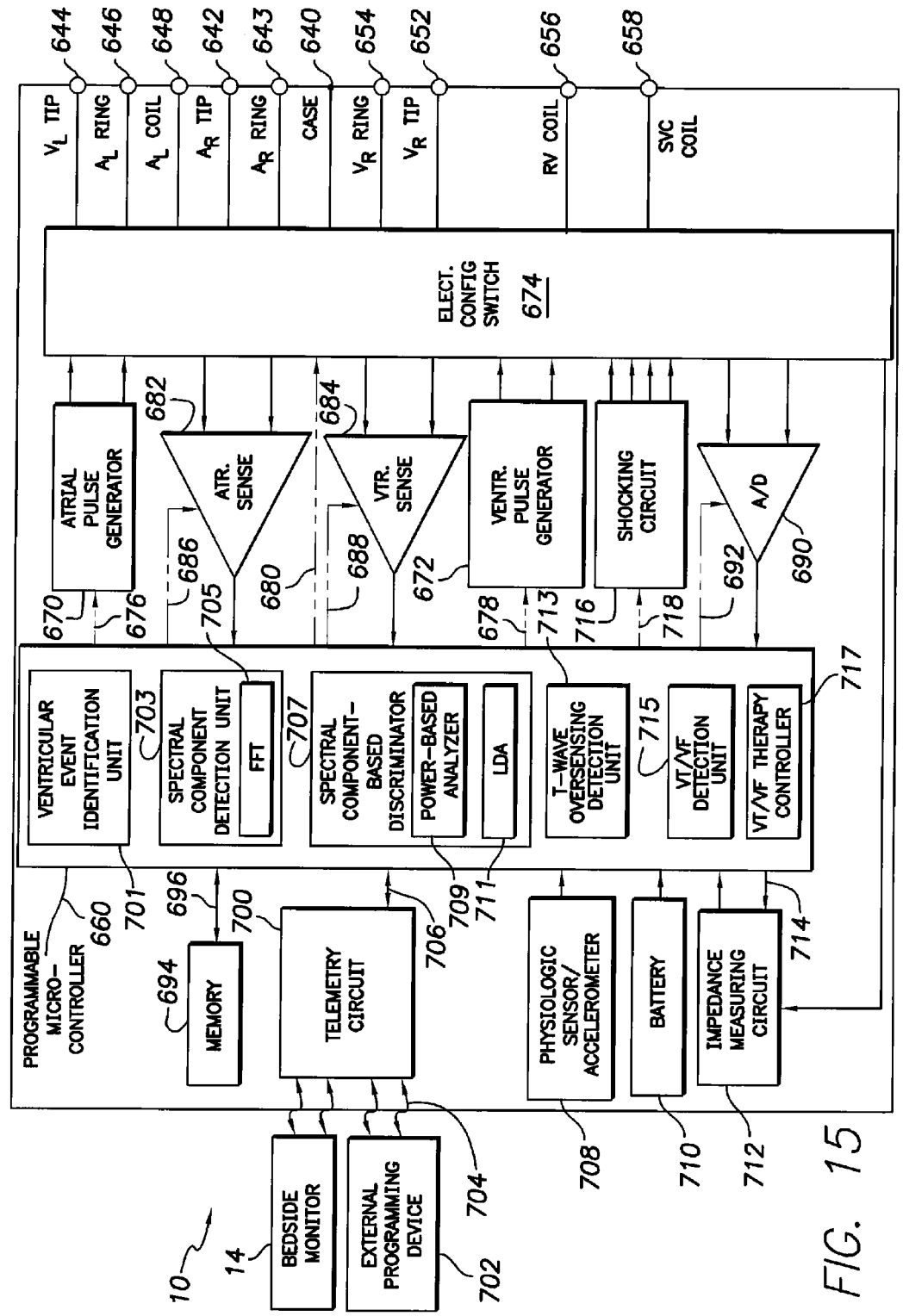
FIG. 15 is a functional block diagram of the pacer/ICD of FIG. 14, illustrating basic circuit elements that provide cardioversion, defibrillation and/or pacing stimulation in four chambers of the heart and particularly illustrating components for distinguishing R-waves from T-wages and for detecting T-wave oversensing in accordance with the techniques of FIGS. 3-13.

A simplified block diagram of internal components of pacer/ICD 10 is shown in FIG. 15. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 640 for pacer/ICD 10, shown schematically in FIG. 15, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 643. To achieve left chamber sensing, pacing and shocking, the connector includes at least a left ventricular tip terminal ($V_L$ TIP) 644, a left atrial ring terminal ($A_L$ RING) 646, and a left atrial shocking terminal ($A_L$ COIL) 648, which are adapted for connection to the left ventricular ring electrode 626, the left atrial tip electrode 627, and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($R_V$ COIL) 656, and an SVC shocking terminal (SVC COIL) 658, which are adapted for connection to the right ventricular tip electrode 632, right ventricular ring electrode 634, the RV coil electrode 636, and the SVC coil electrode 638, respectively.

At the core of pacer/ICD 10 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 15, an atrial pulse generator 670 and a ventricular/impedance pulse generator 672 generate pacing stimulation pulses for delivery by the right atrial lead 620, the right ventricular lead 630, and/or the coronary sinus lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art.

Atrial sensing circuits 682 and ventricular sensing circuits 684 may also be selectively coupled to the right atrial lead 620, coronary sinus lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart. The ventricular sense amplifier 684 preferably includes the aforementioned bradycardia filter, tachycardia filter and wideband filter.

For arrhythmia detection, pacer/ICD 10 utilizes the atrial and ventricular sensing circuits, 682 and 684, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 690. The data acquisition system 690 is configured to acquire intracardiac electrogram signals, convert the raw analog data into a digital signal, and store the digital signals for later processing and/or telemetric transmission to an external device 702. The data acquisition system 690 is coupled to the right atrial lead 620, the coronary sinus lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart. Other pacing parameters include base rate, rest rate and circadian base rate.

Advantageously, the operating parameters of the implantable pacer/ICD 10 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 10 (as contained in the microcontroller 660 or memory 694) to be sent to the external device 702 through an established communication link 704. Pacer/ICD 10 further includes an accelerometer or other physiologic sensor 708, commonly referred to as a "rate-responsive" sensor because it is typically used to adjust pacing stimulation rate according to the exercise state of the patient. However, the physiological sensor 708 may, depending upon its capabilities, further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV Delay, V-V Delay, etc.) at which the atrial and ventricular pulse generators, 670 and 672, generate stimulation pulses. While shown as being included within pacer/ICD 10, it is to be understood that the sensor 708 may also be external to pacer/ICD 10, yet still be implanted within or carried by the patient. A common type of rate responsive sensor is an activity sensor incorporating an accelerometer or a piezoelectric crystal, which is mounted within the housing 640 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 15. The battery 710 may vary depending on the capabilities of pacer/ICD 10. If the system only provides low voltage therapy, a lithium iodine or lithium copper fluoride cell may be utilized. For pacer/ICD 10, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 15, pacer/ICD 10 is shown as having an impedance measuring circuit 712 which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 712 is advantageously coupled to the switch 674 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 6-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Microcontroller 60 also includes various components for implementing or controlling the FFT-based R-wave/T-wave discrimination procedures. A ventricular event identification unit 701 is operative to identify time-varying ventricular event waveforms within signals sensed by the ventricular sense amplifier 684, and particularly within tachycardia-filtered signals. A spectral component detection unit 703 is operative to convert the time-varying event waveforms into frequency-domain waveforms to detect spectral components of the events. This may be achieved using an FFT 703, as discussed above in connection with FIG. 9. A spectral component-based discriminator 705 is operative to distinguish different types of cardiac events based on the spectral components of the events using a power-based analyzer 707 or an LDA 711, or both, as discussed above in connection with FIG. 10. The spectral component-based discriminator 705 is also operative to determine or adjust any necessary comparison parameters, as discussed above in connection with FIG. 11. A T-wave oversensing detection unit 713 is operative to detect T-wave oversensing based on the ventricular depolarization events and the ventricular repolarization events based on, e.g., alternating patterns of T-waves and R-waves, as discussed above in connection with FIG. 13. A VT/VF detection unit 715 is operative to detect ventricular tachyarrhythmias based on R-waves, as discussed above in connection with FIG. 12. A VT/VF therapy controller 717 is operative to control the delivery of therapy in response to ventricular tachyarrhythmias. Depending upon the implementation, the various components illustrated within the microcontroller may be implemented as separate hardware or software modules. However, the modules may be combined so as to permit single modules to perform multiple functions.

What have been described are various exemplary systems and methods for use with an implantable system controlled by a pacer or ICD. However, principles of the invention may be exploiting using other implantable systems or in accordance with other techniques. Thus, while the invention has been described with reference to particular exemplary embodiments, modifications can be made thereto without departing from the scope of the invention. Note also that the term "including" as used herein is intended to be inclusive, i.e. "including but not limited to".

What is claimed is:

1. A method for use by an implantable medical device for implant within a patient for distinguishing cardiac events sensed by the device, said method comprising:
   sensing time-varying electrical cardiac signals within the patient using the device;
   identifying time-varying ventricular electrical cardiac event waveforms therein using the device;
   determining an initial ventricular rate based on all ventricular event waveforms detected within the time-varying signal;
   detecting a possible ventricular tachyarrhythmia within the patient based on a ventricular rate derived from all ventricular events within the time-varying signal by comparing the initial ventricular rate against upper and lower ventricular fibrillation (VF) thresholds;
   if the initial ventricular rate is between the upper and lower VF thresholds, converting the time-varying event waveforms using the device into frequency-domain waveforms to detect spectral components of the events; and
   distinguishing different types of ventricular cardiac events corresponding to individual heartbeats based on the spectral components of the events.

2. The method of claim 1 wherein sensing electrical cardiac signals within the patient includes sensing an intracardiac electrogram (IEGM).

3. The method of claim 1 wherein identifying ventricular event waveforms within the cardiac electrical signals includes filtering the cardiac signals using a tachycardia filter configured to pass cardiac signals appropriate for the detection of tachycardia and identifying any events within the tachycardia-filtered signals as being ventricular events.

4. The method of claim 1 wherein the device includes a time-domain to frequency-domain conversion device and wherein converting the time-varying event waveforms into frequency-domain waveforms includes applying the ventricular event waveforms to the time-domain to frequency-domain conversion device.

5. The method of claim 4 wherein the time-domain to frequency-domain conversion device is a Fourier transform device.

6. The method of claim 1 further including:
   re-determining the ventricular rate based only on ventricular depolarization events (R-waves); and
   delivering defibrillation therapy if the re-determined ventricular rate exceeds the lower VF threshold.

7. The method of claim 6 further including:
comparing the re-determined ventricular rate against a ventricular tachycardia (VT) threshold; and
delivering antitachycardia pacing (ATP) therapy if the re-determined ventricular exceeds the VT threshold but does not exceed the lower VF threshold.

8. The method of claim 1 wherein distinguishing ventricular depolarization events (R-waves) from ventricular repolarization events (T-waves) based on the spectral components of the events includes:
determining an amount of power within an individual cardiac event waveform at frequencies exceeding a predetermined threshold frequency based on the frequency-domain waveform of the event; and
identifying the cardiac event as being a depolarization event if the amount of power above the frequency threshold exceeds a power threshold indicative of a depolarization event and identifying the cardiac event as being a repolarization event otherwise.

9. The method of claim 8 wherein the frequency threshold is set between 10 Hz and 25 Hz.

10. The method of claim 1 wherein distinguishing ventricular depolarization events (R-waves) from ventricular repolarization events (T-waves) based on the spectral components of the events includes:
determining an amount of power within an individual cardiac event waveform at an individual test frequency based on the frequency-domain waveform of the event; and
identifying the cardiac event as being a depolarization event if the amount of power at the test frequency exceeds a power threshold indicative of a depolarization event and identifying the cardiac event as being a repolarization event otherwise.

11. The method of claim 10 wherein the test frequency is set between 25 Hz and 90 Hz.

12. The method of claim 11 wherein the test frequency is about 50 Hz.

13. The method of claim 1 wherein distinguishing ventricular depolarization events (R-waves) from ventricular repolarization events (T-waves) based on the spectral components of the events includes:
determining an amount of power within the cardiac event waveform within a predetermined frequency band based on the frequency-domain waveform of the event; and
identifying the cardiac event as being a depolarization event if the amount of power within the frequency band exceeds a power threshold indicative of a depolarization event and identifying the cardiac event as being a repolarization event otherwise.

14. The method of claim 13 wherein the predetermined frequency band extends from about 30 Hz to about 60 Hz.

15. The method of claim 1 further including an initial step of determining comparison values for use in distinguishing different types of ventricular cardiac events based on the spectral components of the events.

16. The method of claim 15 wherein the comparison values include one or more of frequency threshold values and power threshold values.

17. The method of claim 1:
wherein the device includes a linear discriminant analyzer (LDA) trained to distinguish depolarization events (R-waves) from repolarization events (T-waves); and
wherein distinguishing ventricular depolarization events (R-waves) from ventricular repolarization events (T-waves) based on the spectral components of the events includes applying the frequency domain waveforms of the events to the LDA.

18. The method of claim 17 further including the initial step of training the LDA to distinguish depolarization events (R-waves) from repolarization events (T-waves) within the patient.

19. A method for use by an implantable medical device for implant within a patient for distinguishing cardiac events sensed by the device, said method comprising:
sensing time-varying electrical cardiac signals within the patient using the device;
identifying time-varying ventricular electrical cardiac event waveforms therein using the device;
converting the time-varying event waveforms using the device into frequency-domain waveforms to detect spectral components of the events;
distinguishing different types of ventricular cardiac events corresponding to individual heartbeats based on the spectral components of the events to distinguish ventricular depolarization events (R-waves) from ventricular repolarization events (T-waves);
detecting a quiescent period within the patient;
detecting depolarization events (R-waves) and repolarization events (T-waves) within the quiescent period and power values associated therewith; and
determining suitable comparison values based on characteristics of the depolarization events (R-waves) and repolarization events (T-waves) within the quiescent period and their power values.

20. A method for use by an implantable medical device for implant within a patient for distinguishing cardiac events sensed by the device, said method comprising:
sensing time-varying electrical cardiac signals within the patient using the device;
identifying time-varying ventricular electrical cardiac event waveforms therein using the device;
converting the time-varying event waveforms using the device into frequency-domain waveforms to detect spectral components of the events;
distinguishing different types of ventricular cardiac events corresponding to individual heartbeats based on the spectral components of the events to distinguish ventricular depolarization events (R-waves) from ventricular repolarization events (T-waves); and
detecting the oversensing of ventricular repolarization events (T-waves) within a cardiac signal.

21. The method of claim 20 wherein detecting the oversensing of ventricular repolarization events (T-waves) includes:
identifying a sequence of alternating depolarization events (R-waves) and repolarization events (T-waves) in a cardiac signal; and
associating the sequence of alternating depolarization events (R-waves) and repolarization events (T-waves) in the cardiac signal with T-wave oversensing.

22. An implantable medical device for implant within a patient, said device comprising:
a cardiac signal sensing system operative to sense time-varying electrical cardiac signals within the patient;
an event identification unit operative to identifying time-varying ventricular electrical cardiac event waveforms within the sensed signals;
a spectral component detection unit operative to convert the time-varying event waveforms into frequency-domain waveforms to detect spectral components of the events;

a spectral component-based discriminator operative to distinguish ventricular depolarization events (R-waves) from ventricular repolarization events (T-waves) based on the spectral components of the events; and an oversensing detection unit operative to detect the oversensing of ventricular repolarization events (T-waves) within the cardiac signals.

23. The device of claim 22 wherein the spectral component detection unit includes an FFT device.

24. The system device of claim 22 wherein the spectral component-based discriminator includes a power-based analyzer operative to distinguish ventricular depolarization events (R-waves) from ventricular repolarization events (T-waves) based on power values derived from the spectral components of the events.

25. The device of claim 22 wherein the spectral component-based discriminator includes a linear discriminant analyzer (LDA) operative to distinguish ventricular depolarization events (R-waves) from ventricular repolarization events (T-waves).

26. A method for use by an implantable medical device for implant within a patient for distinguishing cardiac events sensed by the device, said method comprising:

sensing time-varying electrical cardiac signals within the patient using the device;

identifying time-varying ventricular electrical cardiac event waveforms therein;

converting the time-varying event waveforms into frequency-domain waveforms to detect spectral components of the events;

distinguishing ventricular depolarization events (R-waves) from ventricular repolarization events (T-waves) based on the spectral components of the events; and detecting the oversensing of ventricular repolarization events (T-waves) within the cardiac signals following the distinguishing of ventricular depolarization events (R-waves) from ventricular repolarization events (T-waves).

* * * * *